United States Patent [19]
Mochly-Rosen

[11] Patent Number: 6,165,977
[45] Date of Patent: Dec. 26, 2000

[54] ISOZYME-SPECIFIC ACTIVATORS OF PROTEIN KINASE C METHODS AND COMPOSITIONS

[75] Inventor: Daria Mochly-Rosen, Menlo Park, Calif.

[73] Assignee: Board of Trustees of the Leland Stanford Junior University, Stanford, Calif.

[21] Appl. No.: 08/953,033

[22] Filed: Oct. 17, 1997

Related U.S. Application Data

[60] Provisional application No. 60/028,724, Oct. 18, 1996.

[51] Int. Cl.$^7$ .................................................. A61K 38/00
[52] U.S. Cl. ............................... 514/16; 530/328; 435/6; 435/7.8; 435/15; 436/86
[58] Field of Search .............................. 530/328; 514/16; 435/6, 7.8, 15; 436/86

[56] References Cited

U.S. PATENT DOCUMENTS

| | | | |
|---|---|---|---|
| 5,519,003 | 5/1996 | Mochly-Rosen et al. | 514/16 |
| 5,776,685 | 7/1998 | Riedel | 435/6 |
| 5,776,716 | 7/1998 | Ron et al. | 435/15 |
| 5,783,405 | 7/1998 | Mochly-Rosen et al. | 435/15 |
| 5,935,803 | 8/1999 | Vasquez et al. | 435/15 |

FOREIGN PATENT DOCUMENTS

95/21252  8/1995  WIPO.

OTHER PUBLICATIONS

Caplus DN 122:102958, Armstrong et al., Cardiovasc. Res. (1994), 28(11), 1700–6, (abstract).

Brew, Elizabeth, et al., "Role of bradykinin in cardiac functional protection after global ischemia–reperfusion in rat heart," Am. J. Physiol. 269 (Heart Circ. Physiol. 38): H1370–H1378 (1995).

Disatnik, M.-H., et al., "Localization of Protein Kinase C Isozymes in Cardiac Myocytes," Ex. Cell Res. 210:287–297 (1994).

Hu, K., and S. Nattel, "Mechanisms of Ischemic Preconditioning in Rat Hearts," Circulation 92(8): 2259–2265 (1995).

Johnson, J.A., and D. Mochly–Rosen, "Inhibition of the Spontaneous Rate of Contraction of Neonatal Cardiac Myocytes by Protein Kinase C Isozymes A Putative Role for the ϵ Isozyme," Circulation Research 76(4): 654–663 (1995).

Johnson, J.A., et al., "A Protein Kinase C Translocation Inhibitor as an Isozyme–selective Antagonist of Cardiac Function," The Journal of Biological Chemistry 271(40): 24962–24966 (1996).

Liu, G., et al., "Pinacidil but not Nicorandil Opens $K_{ATP}$ Channels in Rabbit Myocytes and Mimics Ischemic Preconditioning," Journal of Molecular and Cellular Cardiology 28(6):T14 (1996).

Liu, Y,. et al., "Pretreatment with Angiotensin II Activates Protein Kinase and Limits Myocardial Infarction in Isolated Rabbit Hearts," J. Mol. Cell Cardiol. 27:883–892 (1995).

Mitchell, M.B., et al., "Protein Kinase C Mediates Preconditioning in Isolated Rat Heart," Circulation 88 (4 part 2): I–633 Abstract No. 3405 (1993).

Mitchell, M.B., et al., "Preconditioning of Isolated Rat Heart Is Mediated by Protein Kinase," Circ. Res. 76(1): 73–81 (1995).

Mochly–Rosen, D., et al., "A protein kinase C isozyme is translocated to cytoskeletal elements on activation," Cell Regulation 1:693–706 (1990).

Mochly–Rosen, D., et al., "Intracellular Receptors for Activated Protein Kinase C," The Journal of Biological Chemistry 266(23): 14866–14868 (1991).

Mochly–Rosen, D., et al., "Identification of intracellular receptor proteins for activated protein kinase C," Proc. Natl. Acad. Sci., 88:3997–4000 (1991).

Mochly–Rosen, D., "Localization of Protein Kinases by Anchoring Proteins: A Theme in Signal Transduction," Science 268: 247–251 (1995).

Moore, Graham, J., "Designing peptide mimetics," TiPS 15124–129 (1994).

Murry, C.E., et al., "Preconditioning with ischemia: a delay of lethal cell injury in ischemic myocardium," Circulation 74(5): 1124–1136 (1986).

Ron, Dorit, et al., "Cloning of an intracellular receptor for protein kinase C: A homolog of the β subunit of G proteins," Proc. Natl. Acad. Sci. USA 91:389–843 (1994).

Ron, Dorit, et al., "C2 Region–derived Peptides Inhibit Translocation and Function of β Protein Kinase C in Vivo," The Journal of Biological Chemistry 270(41):24180–24187 (1995).

Ron, Dorit, and D. Mochly–Rosen, "An autoregulatory region in protein kinase C: The pseudoanchoring site," Proc. Natl. Acad. Sci. USA 92:492–496 (1995).

Schultz, Jo El J., et al., "Morphine Mimics the Cardioprotective Effect of Ischemic Preconditioning via a Glibenclamide–Sensitive Mechanism in the Rat Heart," Circ. Res. 78(6): 1100–1104 (1996).

Smith, B.L., and D. Mochly–Rosen, "Inhibition of Protein Kinase C by Injection of Intracellular Receptors for the Enzyme," Biochem. and Biophys. Res. Com. 188(3):1235–1240 (1992).

Speechly–Dick, M.E., et al., "Protein Kinase C Its Role in Ischemic Preconditioning in the Rat," Circ. Res. 75(3):586–590 (1994).

*Primary Examiner*—Marianne M. Cintins
*Assistant Examiner*—C. Delacroix-Muirheid
*Attorney, Agent, or Firm*—Carol A. Stratford; Judy M. Mohr; Iota Pi Law Group

[57] ABSTRACT

Isozyme-specific agonists or activators of ϵPKC are disclosed. The agonists include peptides corresponding to the region of ϵPKC between about amino acids 85 and 92. Also disclosed are therapeutic methods employing such ϵPKC-specific agonists to induce preconditioning and thereby reduce injury due to subsequent ischemia, as well as methods for screening test compounds for ϵPKC-selective agonist properties.

27 Claims, 9 Drawing Sheets

Fig. 5A αPKC 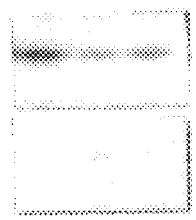
Fig. 5B βPKC
Fig. 5C δPKC 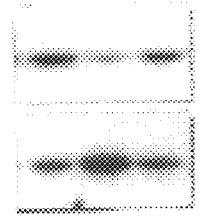
Fig. 5D εPKC 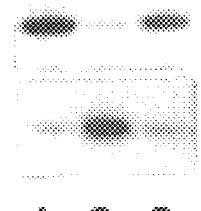

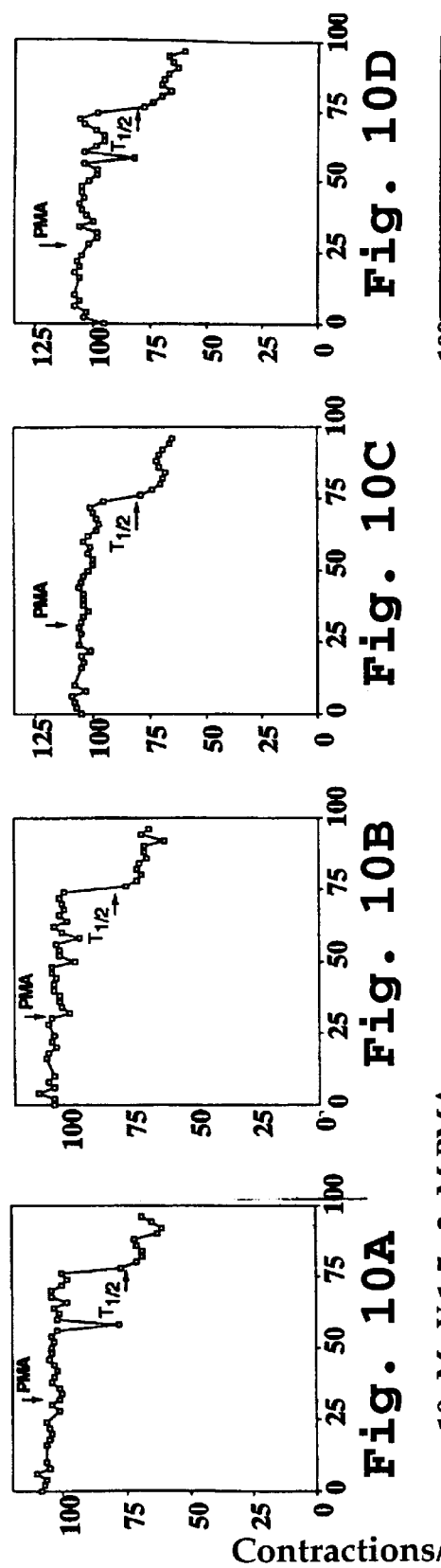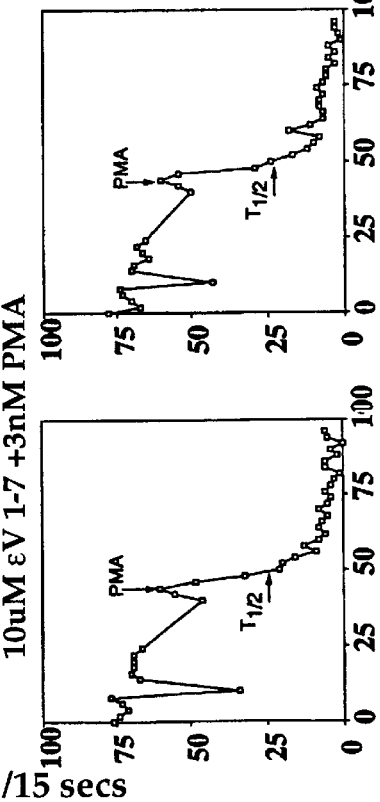

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Other
      (B) LOCATION: 1...9
      (D) OTHER INFORMATION: beta-PKC residues 218-226; betaC2-4

(xi) SEQUENCE DESCRIPTION: SEQ ID NO:1:

Ser Leu Asn Pro Glu Trp Asn Glu Thr
1               5

(2) INFORMATION FOR SEQ ID NO:2:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Other
      (B) LOCATION: 1...6
      (D) OTHER INFORMATION: beta-PKC residues 241-246; betaC2-6

(xi) SEQUENCE DESCRIPTION: SEQ ID NO:2:

Ser Val Glu Ile Trp Asp
1               5

(2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...8
        (D) OTHER INFORMATION: epsilon-PKC residues 14-21; epsilonV1-2

(xi) SEQUENCE DESCRIPTION: SEQ ID NO:3:

Glu Ala Val Ser Leu Lys Pro Thr
 1               5

(2) INFORMATION FOR SEQ ID NO:4:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...7
        (D) OTHER INFORMATION: epsilon-PKC residues 81-87; epsilonV1-3

(xi) SEQUENCE DESCRIPTION: SEQ ID NO:4:

Leu Ala Val Phe His Asp Ala
 1               5

(2) INFORMATION FOR SEQ ID NO:5:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...10
        (D) OTHER INFORMATION: epsilonV1-6; E6

(xi) SEQUENCE DESCRIPTION: SEQ ID NO:5:

Thr Asn Ser Pro Ala Trp His Asp Glu Phe
 1               5                   10

(2) INFORMATION FOR SEQ ID NO:6:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...8
        (D) OTHER INFORMATION: epsilon-PKC residues 85-92;
            epsilonV1-7; E7

(xi) SEQUENCE DESCRIPTION: SEQ ID NO:6:

```
His Asp Ala Pro Ile Gly Tyr Asp
 1               5

(2) INFORMATION FOR SEQ ID NO:7:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...8
        (D) OTHER INFORMATION: epsilonV1-7.1

(xi) SEQUENCE DESCRIPTION: SEQ ID NO:7:

His Asp Ala Pro Ile Gly Asp Tyr
 1               5

(2) INFORMATION FOR SEQ ID NO:8:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...6
        (D) OTHER INFORMATION: epsilonV1-7.2

(xi) SEQUENCE DESCRIPTION: SEQ ID NO:8:

His Asp Ala Pro Ile Gly
 1               5

(2) INFORMATION FOR SEQ ID NO:9:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...8
        (D) OTHER INFORMATION: epsilonV1-7.3

(xi) SEQUENCE DESCRIPTION: SEQ ID NO:9:

His Asp Ala Ala Ile Gly Tyr Asp
 1               5

(2) INFORMATION FOR SEQ ID NO:10:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
```

```
        (B) LOCATION: 1...8
        (D) OTHER INFORMATION: epsilonV1-7.4

(xi) SEQUENCE DESCRIPTION: SEQ ID NO:10:

His Asp Ala Pro Ile Pro Tyr Asp
1               5

(2) INFORMATION FOR SEQ ID NO:11:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...8
        (D) OTHER INFORMATION: epsilonV1-7.5

(xi) SEQUENCE DESCRIPTION: SEQ ID NO:11:

His Asn Ala Pro Ile Gly Tyr Asp
1               5

(2) INFORMATION FOR SEQ ID NO:12:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...8
        (D) OTHER INFORMATION: epsilonV1-7.6

(xi) SEQUENCE DESCRIPTION: SEQ ID NO:12:

His Ala Ala Pro Ile Gly Tyr Asp
1               5

(2) INFORMATION FOR SEQ ID NO:13:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...8
        (D) OTHER INFORMATION: epsilonV1-7.7

(xi) SEQUENCE DESCRIPTION: SEQ ID NO:13:

Ala Asp Ala Pro Ile Gly Tyr Asp
1               5

(2) INFORMATION FOR SEQ ID NO:14:

(i) SEQUENCE CHARACTERISTICS:
        (A) LENGTH: 8 amino acids
        (B) TYPE: amino acid
        (C) STRANDEDNESS: single
        (D) TOPOLOGY: linear
```

```
    (ii) MOLECULE TYPE: peptide (ix) FEATURE:
         (A) NAME/KEY: Other
         (B) LOCATION: 1...8
         (D) OTHER INFORMATION: epsilonV1-7.8

(xi) SEQUENCE DESCRIPTION: SEQ ID NO:14:

His Asp Ala Pro Ala Gly Tyr Asp
 1               5

(2) INFORMATION FOR SEQ ID NO:15:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Other
         (B) LOCATION: 1...8
         (D) OTHER INFORMATION: epsilonV1-7.9

(xi) SEQUENCE DESCRIPTION: SEQ ID NO:15:

His Asp Ala Pro Ile Gly Ala Asp
 1               5

(2) INFORMATION FOR SEQ ID NO:16:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: None
         (B) LOCATION: 1...8
         (D) OTHER INFORMATION: epsilonV1-7.10

(xi) SEQUENCE DESCRIPTION: SEQ ID NO:16:

His Asp Ala Pro Ile Ala Tyr Asp
 1               5

(2) INFORMATION FOR SEQ ID NO:17:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: None
         (B) LOCATION: 1...8
         (D) OTHER INFORMATION: epsilonV1-7.11

(xi) SEQUENCE DESCRIPTION: SEQ ID NO:17:

His Asp Ala Pro Ile Gly Tyr Ala
 1               5

(2) INFORMATION FOR SEQ ID NO:18:
```

```
        (i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 1...8
            (D) OTHER INFORMATION: AplII (xi) SEQUENCE DESCRIPTION: SEQ ID NO:18:

His Asp Ala Ala Ile Pro Pro Asp
  1               5

(2) INFORMATION FOR SEQ ID NO:19:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 1...8
            (D) OTHER INFORMATION: DrosV (xi) SEQUENCE DESCRIPTION: SEQ ID NO:19:

His Asp Ala Ala Leu Pro Pro Asp
  1               5

(2) INFORMATION FOR SEQ ID NO:20:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 1...8
            (D) OTHER INFORMATION: nV1-7

(xi) SEQUENCE DESCRIPTION: SEQ ID NO:20:

His Glu Thr Pro Leu Gly Tyr Asp
  1               5

(2) INFORMATION FOR SEQ ID NO:21:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 1...8
            (D) OTHER INFORMATION: epsilon-RACK2

(xi) SEQUENCE DESCRIPTION: SEQ ID NO:21:

Ala Asn Val Ala Leu Gly Tyr Asp
```

```
                                            -continued
1                       5

(2) INFORMATION FOR SEQ ID NO:22:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...8
        (D) OTHER INFORMATION: epsilon-RACK2.12

(xi) SEQUENCE DESCRIPTION: SEQ ID NO:22:

Asn Asn Val Ala Leu Gly Tyr Asp
1                       5

(2) INFORMATION FOR SEQ ID NO:23:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...14
        (D) OTHER INFORMATION: epsilonV1-7.1x (xi) SEQUENCE DESCRIPTION: SEQ ID NO:23:

Ala Val Phe His Asp Ala Pro Ile Gly Asp Tyr Asp Asp Phe
1                       5                  10
```

ISOZYME-SPECIFIC ACTIVATORS OF PROTEIN KINASE C METHODS AND COMPOSITIONS

This application claims the benefit of U.S. Provisional application Ser. No. 60/028,724, filed Oct. 18, 1996, incorporated herein by reference in its entirety.

This work was supported in part by NIH Grant HL 52141. Accordingly, the United States Government has certain rights in this invention.

FIELD OF THE INVENTION

The present invention relates to isozyme-specific activators of protein kinase C (PKC), particularly activators of εPKC. The invention also relates to methods of treating diseases or conditions which are benefitted by activation of specific isozymes of PKC, particularly, methods of treating cardiac ischemia or stroke by activation of εPKC.

REFERENCES

Ascadi, G., et al., *Nature* 352:815 (1991b).

Ascadi, G., et al., *New Biology* 3:71 (1991a).

Ausubel, F. M., et al., *CURRENT PROTOCOLS IN MOLECULAR BIOLOGY*, John Wiley and Sons, Inc., Media Pa. (1988).

Baines, et al., *J. Mol. Cell. Card.* 28:A158 (1996).

Beck-Sickinger and Jung, *Biopolymers* 37:123–142 (1995).

Berkner, K. L., *BioTechniques* 6:616 (1988).

Betageri, G. V., et al., "Targeting of Liposomes" in *LIPOSOME DRUG DELIVERY SYSTEMS*, Technomic Publishing Co., Inc., Lancaster, Pa., pp 89–108 (1993).

Breakefield, X. O., and DeLuca, N. A., *New Biol.* 3:230 (1992).

Brew, E. C., et al., *Am. J. Physiol.* 269(Heart Circ. Physiol. 38):H1370–H1378 (1995).

Bunin, B. A. and Ellman, J. A., *J. Am. Chem. Soc.* 114:10997 (1992).

Bunin, B. A., et al., *Proc. Natl. Acad. Sci. USA* 91:4708 (1994).

Christiano, R. J., et al., *Proc. Natl. Acad. Sci. U.S.A.* 90:212 (1993).

Csukai, M., et al., *9TH INTERNATIONAL CONFERENCE ON SECOND MESSENGERS AND PHOSPHOPROTEINS* 112 (1995).

Disatnik, M. -H., et al., *Exp. Cell Res.* 210:287–297 (1994).

Escobedo, J. A., et al., *Mol. Cell. Biol.* 11:1125–1132 (1991).

Flugelman, et al., *Circulation* 82:2217 (1990).

Freese, A., et al., *Biochem. Pharm.* 40:2189 (1990).

Goldberg, J., et al., *Eur. J. Biochem.* 218:597–601 (1993).

Gottlieb, R. A., et al., *J. Clin. Invest.,* 94:1612–1628 (1994).

Graham, F. L., and Prevea, L., in *METHODS IN MOLECULAR BIOLOGY*, Vol. 7 (Murray, E. J., Ed.) Humana, Clifton, N.J., pp. 109–127 (1991).

Grunhaus, A. and Horowitz, M. S., *Semin. Virol.,* 3:237–252 (1992).

Hansen, P. R., and Stawaski, G., *Cardiovasc. Res.,* 28:565–569 (1994).

Hari, et al., *Endocrinology* 120:829–831 (1987).

Hauser, J. M. L., et al., *J. Biol. Chem.* 269:6803–6809 (1993).

Hertz, J., and Gerard, R. D., *Proc. Natl. Acad. Sci. U.S.A.* 90:2812–2816 (1993).

Hu, K. and Nattel, S., *Circulation* 92:2259–2265 (1995).

Jaffe, H. A., et al., *Nat. Genet.* 1:374 (1992).

Jones, N., and Shenk, T., *Cell* 16:683 (1979).

Johnson, J. A., and Mochly-Rosen, D., *Circ. Res.* 76:654–663 (1995).

Johnson, J. A., et al., *J. Biol. Chem.* 271:24962–24966 (1996).

Kasahara, N., et al., *Science* 266:1373 (1994).

Kass-Eisler, et al., *Proc. Natl. Acad. Sci.* 90:11498–11502 (1993).

Kennedy, P. G., and Steiner, I., *Q.J. Med.* 86:697–702 (1993).

Khandoudi, et al., *J. Mol. Cell. Card.* 28:A165 (1996).

Kirshenbaum, L. A., et al., *J. Clin. Invest.* 92:381 (1993).

Kirshenbaum, L. A., and Schneider, M. D., *J. Biol. Chem.* 270:7791–7794 (1994).

Kitsis, R., et al., *Proc. Natl. Acad. Sci. U.S.A.* 88:4138 (1991).

Kloner, R. A., et al., *Circulation* 91:37–45 (1995).

Kloner, R. A., and Yellon, D., *J. Am. Coll. Cardiol.* 24:1133–1142 (1994).

Leclere, G., et al., *J. Clin. Invest.* 90:936 (1992).

Lefer, et al., *Circulation* 88:1779–1787 (1994).

Lin, H., et al., *Circulation* 82:2217 (1990).

Link, R. E., et al., *Science* 273:803 (1996).

Liu, G., et al., *J. Mol. Cell. Card.* 28:T14 (1996).

Liu, Y., et al., *J. Mol. Cell. Cardiol.* 27:883–892 (1995).

Liu, Y., et al., *Circ. Res.* 78:443–454 (1996).

Miller, A. D., *Hum. Gene Ther.* 1:5 (1990).

Mitchell, M. B., et al., *Circulation* 88:1633 (1993).

Mitchell, M. B., et al., *Circ. Res.* 76:73–81 (1995).

Mochly-Rosen, D., et al., *Molec. Biol. Cell* (formerly *Cell Reg.*), 1:693–706 (1990).

Mochly-Rosen, D., et al., *Proc. Natl. Acad. Sci. USA* 88:3997–4000 (1991).

Mochly-Rosen, D., *Science* 268:247–251 (1995).

Moore, G. J., *Trends in Pharmacological Sciences* 15:124–129 (1994).

Murry, C. E., et al., *Circulation* 74:1123–1136 (1986).

Nabel, E. G., et al., *Science* 249:1285 (1990).

Nagashima, M., et al., *J. Biol. Chem.* 268:2888–92 (1993).

Papadopoulos, V., and Hall, P. F., *J. Cell Biol.* 108:553–567 (1989).

Pitcher, J., et al., *Science* 257:1264–1267 (1992).

Quantin, B., et al., *Proc. Natl. Acad. Sci. U.S.A.* 89:2581 (1992).

Rocha-Singh, K. J., et al., *J. Clin. Invest.* 88:204–213 (1991).

Ron, D., et al., *Proc. Natl. Acad. Sci. USA* 91:839–843 (1994).

Ron, D., et al., *J. Biol. Chem.* 279:24180–24187 (1995a).

Ron, D., et al., *Proc. Natl. Acad. Sci. USA* 92:492–496 (1995b).

Rosenfeld, M. A., et al., *Science* 252:431 (1991).

Rosenfeld, M. A., et al., *Cell*, 68:143–155 (1992).

Saito, N., et al., *Proc. Natl. Acad. Sci. USA* 86:3409–3413 (1989).

Sambrook, J., et al., *MOLECUAR CLONING: A LABORATORY MANUAL*, Second Edition, Cold Spring Harbor Laboratory, Cold Spring Harbor, N.Y., (1989).

Schulz, G. E., and Schirmer, R. H., in *PRINCIPALS OF PROTEIN STRUCTURE*, Springer-Verlag (1979).

Schultz, J. E. J., et al., *Circ. Res.* 78:1100–1104 (1996).

Shao, X., et al., *Science* 273:248–251 (1996).

Simpson, P. C., et al., *Circ. Res.* 51:787–801 (1982).

Smith, B. L., and Mochly-Rosen, D., *Biochem. Biophys. Res. Commun.* 188:1235–1240 (1992).

Smith, D. B., et al., *Gene* 67:31 (1988).

Speechly-Dick, M. E., et al., *Circ. Res.* 75:586–590 (1993).

Stratford-Perricaudet, L. D., et al., *J. Clin. Invest.* 90:626 (1992a).

Stratford-Perricaudet, L. D., et al., *Bone Marrow Transplant* 9(suppl. 1):151 (1992b).

Thornton, J. D., et al., *J. Mol. Cell Cardiol.* 25:311 (1993).

Virgilio, A. A., and Ellman, J. A., *J. Am. Chem. Soc.* 116:11580 (1994).

Wagner, E., et al., *Proc. Natl. Acad. Sci. U.S.A.* 89:6099 (1992a).

Wagner, E., et al., *Proc. Natl. Acad. Sci. U.S.A.* 89:7934 (1992b).

Wolf, A., et al., *Science* 247:1465 (1990).

Wu, G. Y., *J. Biol. Chem.* 266:14338 (1991).

Youker, et al., *J. Clin. Invest.* 89:602–609 (1992).

Yung, W. K., *Curr. Opin. Oncol.* 6:235–239 (1994).

Zhang, L. X., et al., *Neuroreport*, 3:700 (1992).

BACKGROUND OF THE INVENTION

Despite recent advances in the understanding of the molecular basis of ischemic heart disease, heart disease and stroke remain the leading cause of death in the United States, accounting for $151 billion in medical expenses and lost productivity in 1996. Heart attacks alone are responsible for 500,000 deaths annually in this country and 14.3 million deaths worldwide. Although half of these deaths occur suddenly and out-of-hospital, half occur in patients who do reach a medical facility.

In addition, close to 700,000 individuals in this country have non-fatal heart attacks. These individuals are at substantially greater risk for subsequent episodes of ischemia, which in many cases prove debilitating or fatal.

Improved pharmacologic methods for protection of the ischemic myocardium could be life-saving for both the surviving victims of heart attacks, as well as those who now die after reaching a hospital.

SUMMARY OF THE INVENTION

In one aspect, the present invention includes an εPKC agonist peptide, such as a peptide having a sequence selected from the group consisting of SEQ ID NO:6, SEQ ID NO:7, SEQ ID NO:8, SEQ ID NO:9, SEQ ID NO:10, SEQ ID NO:12, SEQ ID NO:13, SEQ ID NO:14, SEQ ID NO:15, SEQ ID NO:16, SEQ ID NO:17, SEQ ID NO:18, and SEQ ID NO:19. In one embodiment, the peptide has a sequence selected from the group consisting of SEQ ID NO:6, SEQ ID NO:7, SEQ ID NO:8, SEQ ID NO:9, SEQ ID NO:10, SEQ ID NO:12, SEQ ID NO:13 and SEQ ID NO:18. In another embodiment, the peptide has a sequence selected from the group consisting of SEQ ID NO:6, SEQ ID NO:7, SEQ ID NO:8, SEQ ID NO:9, SEQ ID NO:10 and SEQ ID NO:18. In one specific embodiment, the peptide has the sequence represented by SEQ ID NO:6. In another specific embodiment, the peptide has the sequence represented by SEQ ID NO:7. In yet another specific embodiment, the peptide has the sequence represented by SEQ ID NO:8. In still other embodiments, the peptide has a sequence derived from and corresponding to one of the above sequences, but containing conservative amino acid substitutions.

In one general embodiment, the peptide is between about 4 and 30 amino acids in length. In another general embodiment, the peptide is between about 5 and about 15 amino acids in length. Preferably, the peptide is between about 6 and about 10 amino acids in length.

The peptide may be (i) chemically synthesized or (ii) recombinantly produced in a host cell using, e.g., an expression vector containing a polynucleotide fragment encoding said peptide, where the polynucleotide fragment is operably linked to a promoter capable of expressing mRNA from the fragment in the host cell.

In another aspect, the invention includes a method of reducing ischemic injury to a cell exposed to hypoxic conditions. The method includes introducing into the cell, prior to exposure to hypoxic conditions, a pharmaceutically-effective amount of an isozyme-specific εPKC agonist. The εPKC agonist stimulates εPKC, resulting in preconditioning of the cell. The preconditioning in turn is effective to reduce ischemic injury to the cell caused by a subsequent exposure to ischemic conditions. The amount of reduction of ischemic injury is measured relative to the ischemic injury suffered by a corresponding cell that did not undergo preconditioning.

In one general embodiment, isozyme-specific εPKC agonist is a peptide, such as an εPKC agonist peptide. Exemplary εPKC agonist peptides include peptides having a sequence selected from the group consisting of SEQ ID NO:6, SEQ ID NO:7, SEQ ID NO:8, SEQ ID NO:9, SEQ ID NO:10, SEQ ID NO:12, SEQ ID NO:13, SEQ ID NO:14, SEQ ID NO:15, SEQ ID NO:16, SEQ ID NO:17, SEQ ID NO:18, and SEQ ID NO:19, in particular, peptides having a sequence selected form the group consisting of SEQ ID NO:6 and SEQ ID NO:7.

The method can be practiced with a variety of cell types, including cardiac cells, central nervous system (CNS) cells (e.g., neurons, glial cells), kidney cells and the like. In another general embodiment, the εPKC agonist is introduced using a carrier or encapsulant, such as a liposome in liposome-mediated delivery.

In yet another aspect, the invention includes a method of identifying a compound effective to induce preconditioning. This method includes the steps of (i) contacting an εPKC polypeptide containing a RACK binding site with an εPKC agonist peptide in the presence and absence of a test compound, (ii) measuring the effect of the test compound on the extent of binding between the εPKC polypeptide and the agonist peptide, and (iii) identifying the compound as effective if its measured effect on the extent of binding is above a threshold level.

In one general embodiment, the test compound is effective to inhibit binding between the εPKC polypeptide and the agonist peptide. In another general embodiment, the test compound is effective to displace the peptide from the polypeptide. Yet another general embodiment includes immobilizing the εPKC polypeptide on a solid support, either by simply allowing it to adhere to, e.g., a plastic well, or via suitable chemical coupling moieties which are well-known in the art. In one embodiment, the test compound is one of a plurality of small molecules in a small molecule combinatorial library.

The polypeptide used in the method may be a full-length εPKC polypeptide or only a fragment, where the fragment contains at least εPKC amino acids 1–142. As above, the isozyme-selective agonist peptide has, in one embodiment, a sequence selected from the group consisting of SEQ ID NO:6, SEQ ID NO:7, SEQ ID NO:8, SEQ ID NO:9, SEQ ID NO:10, SEQ ID NO:12, SEQ ID NO:13, SEQ ID NO:14, SEQ ID NO:15, SEQ ID NO:16, SEQ ID NO:17, SEQ ID NO:18, and SEQ ID NO:19.

To allow detection of the degree of binding, the peptide is typically labelled with a reporter, such as a fluorescent or radioactive tag. Molecular Probes (Eugene, Oreg.), provides reagents for flourescently-labelling peptide and proteins, as well as custom labelling services. Protocols for radiolabelling peptides are known (e.g., Ausubel, et al., 1988).

These and other objects and features of the invention will become more fully apparent when the following detailed description is read in conjunction with the accompanying drawings.

BRIEF DESCRIPTION OF THE FIGURES

FIG. 1A shows myocytes maintained under normoxic conditions, and FIG. 1B shows myocytes following 9 hours of hypoxia.

FIGS. 5A–5D show Western Blot analyses of the PMA-induced translocation of different PKC isoforms from the cell soluble to the cell particulate fractions.

FIGS. 10A–10H show the effects of peptide εV1-7 and PMA on cardiac cell contraction rates. FIGS. 10A–D show results of experiments with sham-skinned cells #1–#4, respectively, and FIGS. 10E–H show results of experiments with experimental cells #1–#4, respectively.

DETAILED DESCRIPTION OF THE INVENTION

I. Definitions

Figure 1A:
FIGS. 1A and 1B show the results of a fluorescence-based assay of cardiac myocyte viability.

"Ischemia" is defined as an insufficient supply of blood to a specific organ or tissue. A consequence of decreased blood supply is an inadequate supply of oxygen to the organ or tissue (hypoxia). Prolonged hypoxia may result in injury to the affected organ or tissue. "Anoxia" refers to a virtually complete absence of oxygen in the organ or tissue, which, if prolonged, may result in death of the organ or tissue.

"Hypoxic condition" is defined as a condition under which a particular organ or tissue receives an inadequate supply of oxygen.

"Anoxic condition" refers to a condition under which the supply of oxygen to a particular organ or tissue is cut off.

"Ischemic injury" refers to cellular and/or molecular damage to an organ or tissue as a result of a period of ischemia.

The term "significant", when used with reference to "significantly different", "significantly inhibits" or "significantly stimulates", refers to a difference in a quantifiable parameter between the two groups being compared that is statistically-significant using standard statistical tests. For example, the degree of binding in a protein binding assay may be quantified using standard methods, and the degree of binding under different conditions can be compared for statistically-significant differences.

"Treating" a disease refers to administering a therapeutic substance effective to reduce the symptoms of the disease and/or lessen the severity of the disease.

"Conservative amino acid substitutions" are substitutions which do not result in a significant change in the activity (e.g., εPKC-agonist activity) or tertiary structure of a selected polypeptide. Such substitutions typically involve replacing a selected amino acid residue with a different residue having similar physico-chemical properties. For example, substitution of Glu for Asp is considered a conservative substitution since both are similarly-sized negatively-charged amino acids. Groupings of amino acids by physico-chemical properties are known to those of skill in the art and can be found, for example, in Schulz and Schirmer (1979).

With respect to a specific sequence, "conservative substitutions thereof" refers to sequences that differ from the specific sequence by having conservative amino acid substitutions at one or more positions.

When a first peptide or polypeptide fragment is said to "correspond" to a second peptide or polypeptide fragment, it means that the fragments or regions thereof are essentially co-extensive with one another when the sequences representing the fragments are aligned using a sequence alignment program, such as "MACVECTOR" (IBI, New Haven, Conn.). "Corresponding" peptide or polypeptide fragments typically contain a similar, if not identical, number of residues. It will be understood, however, that corresponding fragments may contain insertions or deletions of residues with respect to one another, as well as some differences in their sequences.

A polypeptide sequence or fragment is "derived" from another polypeptide sequence or fragment when it has the same sequence of amino acid residues as the corresponding region of the fragment from which it is derived.

An "εPKC agonist peptide" or "εPKC specific agonist peptide" is understood to mean a peptide between about 4 and about 30, preferably between about 5 and about 15, amino acids in length that is derived from the region of εPKC between about amino acids 70 and 120, preferably between about amino acids 80 and 100, more preferably between about amino acids 85 and 92. At least a portion of said εPKC agonist peptide overlaps with the region of εPKC corresponding to SEQ ID NO:8. An exemplary εPKC agonist peptide is peptide εV1-7 (SEQ ID NO:6).

An "εPKC polypeptide containing a RACK binding site" is understood to mean a full-length εPKC polypeptide or fragment thereof, where the fragment contains the portion of εPKC between about amino acids 1 and 142.

II. Protein Kinase C and Cardiac Preconditioning

A. Protein Kinase C

Protein kinase C (PKC) is a key enzyme in signal transduction involved in a variety of cellular functions, including cell growth, regulation of gene expression and ion channel activity. The PKC family of isozymes includes at least 11 different protein kinases which can be divided into at least three subfamilies based on their homology and sensitivity to activators. Members of the classical or αPKC subfamily, α, $β_I$, $β_{II}$ and γPKC, contain four homologous domains (C1, C2, C3 and C4) inter-spaced with isozyme-unique (variable or V) regions, and require calcium, phosphatidylserine (PS), and diacylglycerol (DG) or phorbol esters for activation. Members of the novel or nPKC subfamily, δ, ε, η, and θPKC, lack the C2 homologous domain and do not require calcium for activation. Finally, members of the atypical or αPKC subfamily, ξ and λ/τPKC, lack both the C2 and one half of the C1 homologous domains and are insensitive to DG, phorbol esters and calcium.

Studies on the subcellular distribution of PKC isozymes demonstrate that activation of PKC results in its redistribution in the cells (also termed translocation), such that activated PKC isozymes associate with the plasma membrane, cytoskeletal elements, nuclei, and other subcellular compartments (Saito, et al., 1989; Papadopoulos and Hall, 1989; Mochly-Rosen, et al., 1990).

It appears that the unique cellular functions of different PKC isozymes are determined by their subcellular location. For example, activated $β_I$PKC is found inside the nucleus, whereas activated $β_{II}$PKC is found at the perinucleus and cell periphery of cardiac myocytes (Disatnik, et al., 1994). Further, in the same cells, εPKC binds to cross-striated structures (possibly the contractile elements) and cell-cell contacts following activation or after addition of exogenous activated εPKC to fixed cells (Mochly-Rosen, et al., 1990; Disatnik, et al., 1994). The localization of different PKC isozymes to different areas of the cell in turn appears due to binding of the activated isozymes to specific anchoring molecules termed Receptors for Activated C-Kinase (RACKs).

RACKs are thought to function by selectively anchoring activated PKC isozymes to their respective subcellular sites. RACKs bind only fully activated PKC, but RACKs are not necessarily substrates of the enzyme nor is the binding to RACKs mediated via the catalytic domain of the kinase (Mochly-Rosen, et al., 1991). Translocation of PKC reflects binding of the activated enzyme to RACKs anchored to the cell particulate fraction and the binding to RACKs is required for PKC to produce its cellular responses (Mochly-Rosen, 1995). Inhibition of PKC binding to RACKs in vivo inhibits PKC translocation and PKC-mediated function (Johnson, et al., 1996; Ron, et al., 1995a; Smith and Mochly-Rosen, 1992).

cDNA clones encoding RACK1 and RACK2 have been identified (U.S. Pat. No. 5,519,003; Ron, et al., 1994; Csukai, et al., 1995). Both are homologs of the β subunit of G proteins, a receptor for another translocating protein kinase, the β-adrenergic receptor kinase, βARK (Pitcher, et al., 1992). Similar to Gβ, RACK1 and RACK2 have seven WD40 repeats (Ron, et al., 1994; Csukai, et al., 1995). Recent data suggest that RACK1 is a $β_{II}$PKC-specific RACK whereas RACK2 is specific for activated εPKC.

Translocation of PKC is required for proper function of PKC isozymes. Peptides that mimic either the PKC-binding site on RACKs (Mochly-Rosen, 1995) or the RACK-binding site on PKC (Ron, et al., 1995a; Johnson, et al., 1996) are isozyme-specific translocation inhibitors of PKC that selectively inhibit the function of the enzyme in vivo. Specifically, as described in more detail below, an eight amino acid peptide derived from εPKC (peptide εV1-2; SEQ ID NO:3) that contains at least part of the RACK-binding site on εPKC selectively inhibits specific εPKC-mediated functions in cardiac myocytes. In contrast, βPKC-derived peptides corresponding to the RACK-binding site in cPKCs (e.g., peptide βC2-4; SEQ ID NO:1; a βPKC-specific antagonist), do not modulate these functions (Johnson, et al., 1996).

B. Protective Preconditioning

Prolonged ischemia causes irreversible myocardium damage primarily due to death of cells at the infarct site. Studies in animal models, isolated heart preparations and isolated cardiac myocytes in culture have demonstrated that short bouts of ischemia of cardiac muscle reduce such tissue damage in subsequent prolonged ischemia (Liu, Y., et al., 1995, 1996; Hu, et al., 1995; Brew, et al., 1995; Schultz, et al., 1996). This protection, which occurs naturally following angina and has been termed preconditioning, can be mimicked by a variety of non-specific PKC agonists (Mitchell, et al., 1993; Mitchell, et al., 1995; Murry, et al., 1986; Speechly-Dick, et al., 1994). Prior to the teachings herein, it was not clear which of the at least seven PKC isozymes present in the heart are responsible for the preconditioning process. Further, no isozyme-specific agonists which might be useful in achieving such preconditioning were known.

Figure 6A:
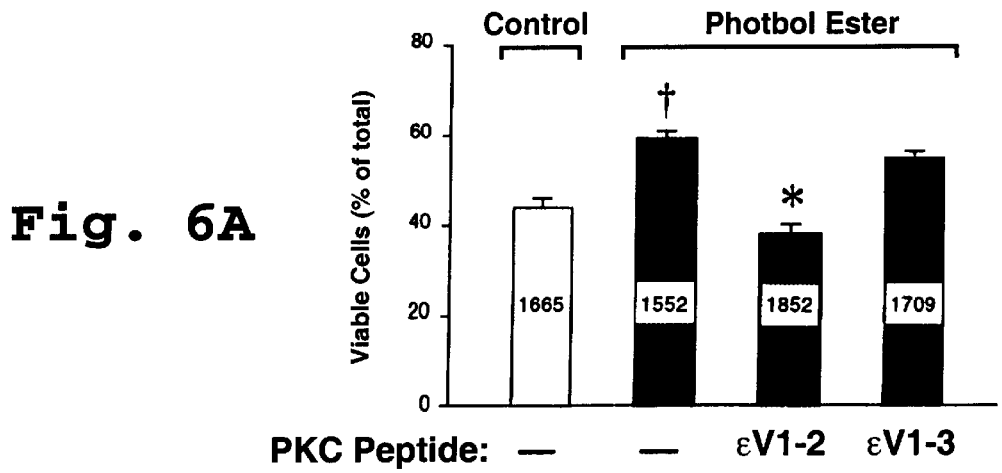
FIGS. 6A and 6B show PMA- (FIG. 6A) or preconditioning- (FIG. 6B) induced protection of cardiac myocytes from subsequent prolonged hypoxia in the presence and absence of isoform-specific inhibitory peptides.
Figure 6B:
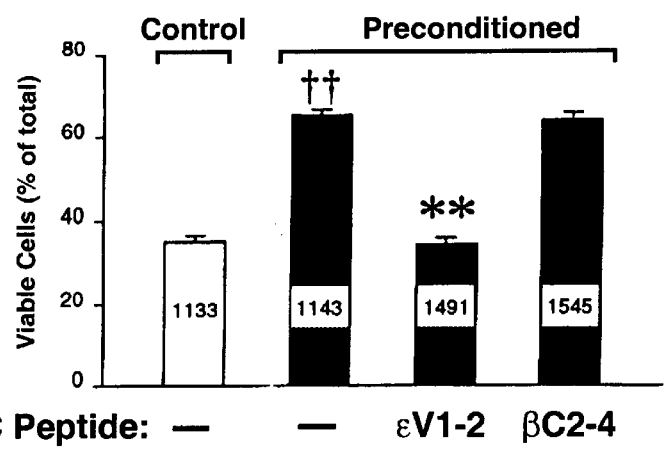

Experiments performed in support of the present invention have identified a specific isozyme of PKC that mediates preconditioning, as well as a class of isozyme-specific agonists which can be administered to activate it. The results described herein show that while both δ and εPKC activation occurs following preconditioning, εPKC activation is required for protection of cardiac myocytes from ischemia-induced cell death (see, e.g., Example 4), since this protection was completely abolished in the presence of the εPKC-selective translocation antagonist peptide εV1-2 (FIGS. 6A and 6B).

Figure 8:
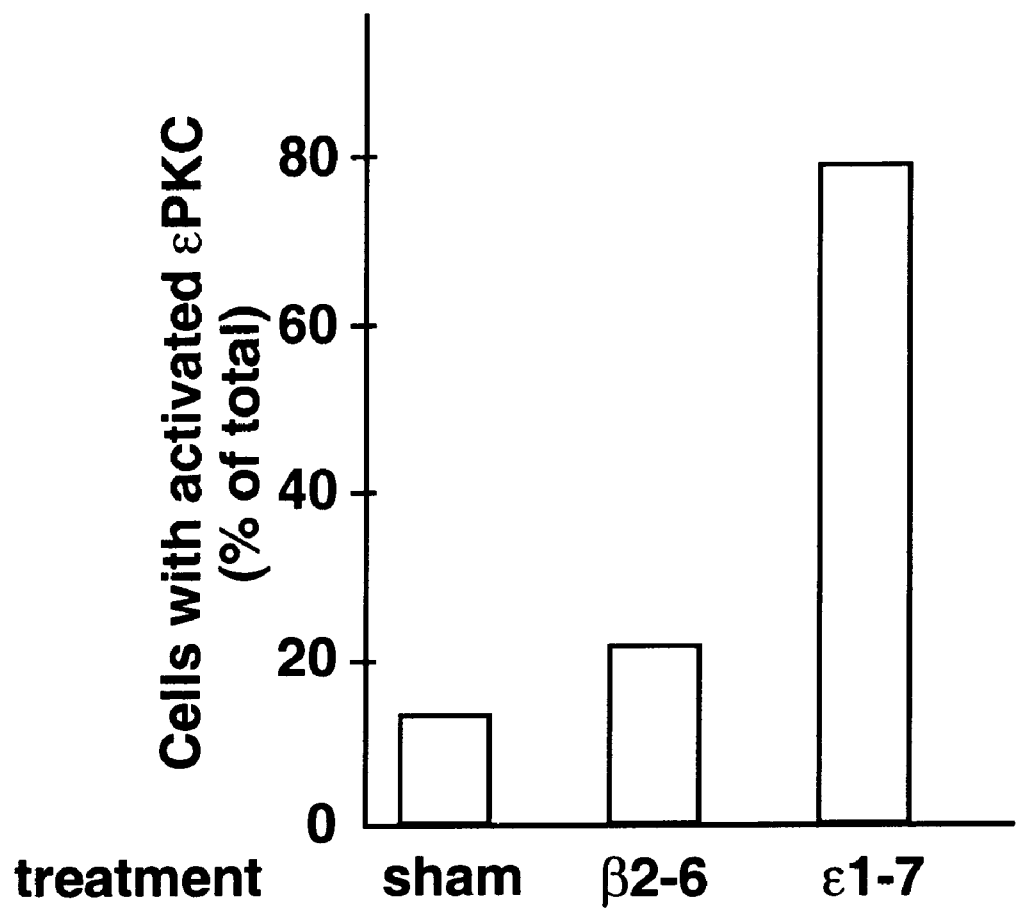
FIG. 8 shows the percent of cells in which εPKC was activated by either peptide β2-6 (SEQ ID NO:2) or εV1-7 (SEQ ID NO:6).
Figure 9:
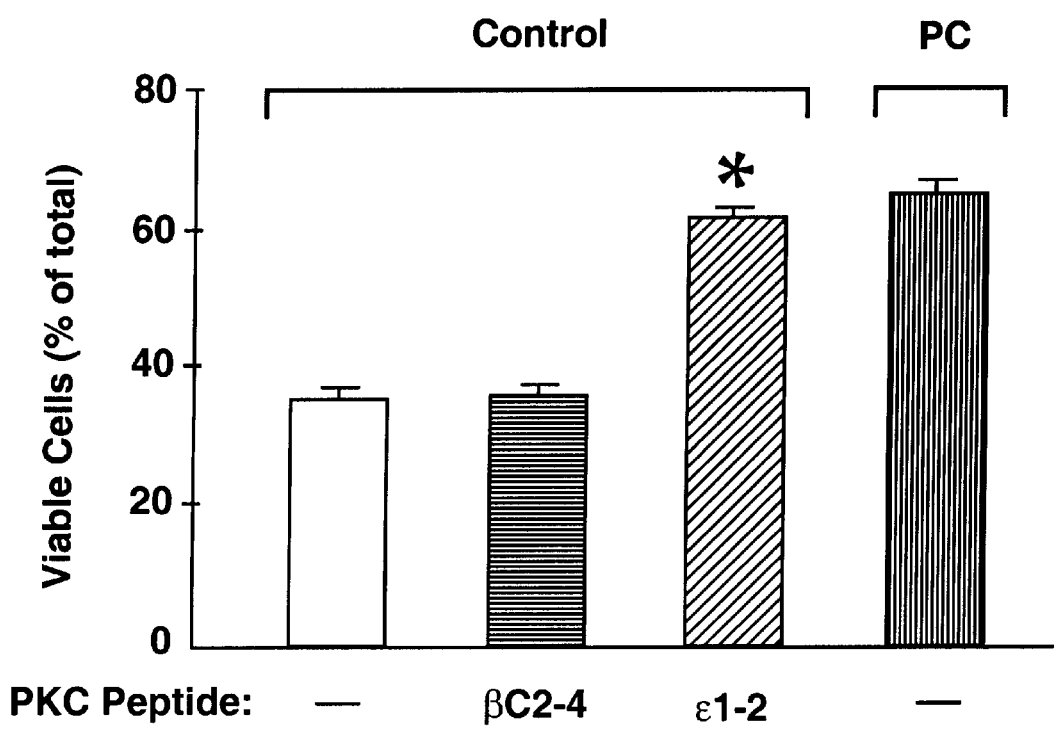
FIG. 9 shows the degree of cytoprotection from subsequent hypoxia afforded by peptides βC2-4 and εV1-7.

Further, the results described herein demonstrate that an εPKC-selective agonist (peptide εV1-7; SEQ ID NO:6) causes εPKC translocation in the absence of hormone or preconditioning stimulation (FIG. 8) and mimics preconditioning by protecting cardiac myocytes from hypoxia-induced cell death (FIG. 9).

III. Selection of Protein Activation Domains

According to the present invention, peptides capable of activating signalling proteins (such as PKC), which in vivo are activated by binding to a cognate polypeptide such as a receptor protein (e.g., a RACK), can be identified using the approach detailed below.

The approach is best suited to situations where the sequences of both the effector protein and the receptor are known. Sequences suitable for the construction of such peptides are identified as short (about 6–12 amino acids) regions of homology between the signaling protein and its cognate molecule. This region is likely to contain at least one non-conserved amino acid substitution. The rationale for this approach is based on the observation that certain signalling proteins (e.g., PKC) contain domains which are similar in sequence to regions of the cognate polypeptide involved in binding to the signalling protein. In PKC, these regions are termed "pseudo-RACK" sequences (Ron, et al., 1994, 1995b), since their sequence is similar to the PKC-binding region of the corresponding RACK.

A synthetic peptide corresponding to this sequence is expected to mimic activation of that signaling molecule in vitro and to act as an agonist of the molecule in vivo.

To identify such an activating peptide for a signalling molecule whose cognate polypeptide is not known, or for a signalling molecule that has not been isolated but for which there exists a known isolated cognate polypeptide, the unknown polypeptide partner must be isolated and identified. Several approaches exist for the isolation of such interacting proteins. For example, monoclonal antibodies raised to the known protein or polypeptide may be used to co-precipitate the other interacting protein (Hari, et al., 1987; Escobedo, et al., 1991).

An alternate method to identify unknown polypeptides that interact with a known, isolated protein is by the use of, for example, an overlay assay (Wolf, et al., 1990; Mochly-Rosen, et al., 1991). A mixture (such as a fraction of a tissue homogenate, for example, a Triton-insoluble protein fraction) potentially containing proteins that bind to a known, isolated protein can be resolved using PAGE, blotted onto a nitrocellulose or nylon membrane, and contacted with a solution containing the known protein and any necessary co-factors or small molecules. After washing, the membrane can be contacted with a probe for the known protein, for example an antibody or a mixture of antibodies, and the signal visualized.

Alternatively or in addition to the biochemical approaches described above, molecular approaches may be used to isolate DNA clones encoding the interacting proteins of interest. Such clones may be identified, for example, by screening an appropriate cDNA expression library. Expression libraries made from a wide variety of tissues are commercially available (for example, from Clontech, Palo Alto, Calif.). Expression libraries may also be made de novo from organisms and tissues of choice by practitioners skilled in the art.

The screening of expression libraries for clones expressing a protein or protein fragment of interest may be readily accomplished using techniques known in the art, for example, an overlay assay. An overlay-assay screening method may be used to identify clones expressing a (known or unknown) protein or protein fragment that binds to a probe in hand. The probe may be a protein postulated to be involved in protein—protein interactions with a protein expected to be present in a cDNA library selected for screening.

Actual screening of a selected cDNA library may be accomplished by inducing plated clones to express cloned exogenous sequences, transferring replicas of the induced plaques or colonies to filter membranes, and screening the membranes with an appropriate probe. According to this method, lifts of filters (for example, nylon or nitrocellulose) from an appropriately-induced cDNA library plates (induced by, for example, IPTG) are washed, blocked, and incubated with a selected probe for a period of time sufficient to allow the selected probe(s) to bind specifically to polypeptide fragments present on the filters. The filters may then be washed and reacted with a reagent (for example, antibodies such as alkaline phosphatase-conjugated goat anti-rabbit or anti-mouse antibodies, available from Boehringer Mannheim Biochemicals, Indianapolis, Ind.). Additional reactions may be carried out as required to detect the presence of bound probe.

Once a clone or clones are identified in a screen such as one described above, the clones are purified (for example, plaque purified), and cDNA inserts are isolated by standard methods. The inserts may be sequenced and used in subsequent cloning reactions.

When a putative clone is identified, it can be isolated or plaque purified and sequenced. The insert may then be used in other cloning reactions, for example, cloning into an expression vector that enables efficient production of recombinant fusion protein. Examples of appropriate expression vectors are pGEX (Smith, et al., 1988) and pMAL-c2 (New England BioLabs, Beverly, Mass.). An expression vector containing an insert of interest may be used to transform appropriate host cells, such as *E. coli,* and the transformed host cells can be used to produce the recombinant protein in large amounts.

Typically, a recombinant protein is expressed in tandem with a bacterial or viral gene product (endogenous polypeptide) as part of a fusion protein. The junction between the endogenous polypeptide and the recombinant protein typically includes a recognition site for a rare-cutting protease. The endogenous peptide may be designed to incorporate a unique affinity tag (a short peptide sequence) to facilitate the purification of the fusion protein with an affinity reagent, such an antibody directed against the affinity tag. The recombinant protein may then be purified from the fusion protein using the appropriate protease.

Regions of homology between the signaling protein and its cognate molecule can be determined in any of a number of ways known to those skilled in the art. One widely-implemented computer-assisted method is to generate a cross-homology matrix. A cross-homology matrix computes the similarity of sequential amino acid residues in a particular sequence with corresponding sequential residues in the other sequence. The similarity scores are stored in a 2-dimensional matrix. Values higher than a selected criterion level are flagged and displayed as points on an x-y coordinate. The x- and y-axes correspond to consecutive amino acid positions in the two sequences, respectively.

Most sequence comparison programs provide an option for performing homology matrix analyses. One example is the computer program DNA Strider 1.2 (Christian Marck, Service de Biochemie et de Genetique Moleculaire, Department de Biologie Cellulaire et Moleculaire, Direction des Sciences de la Vie—CEA—FRANCE).

Regions of sequence similarity obtained using a cross-homology matrix may further be directly compared at the sequence level by eye or on a personal computer using, for example, a text editor, a drawing program or a sequence-analysis program. Examples of programs effective to accomplish an alignment include "MACDRAW PRO" (Claris Corp., Santa Clara, Calif.) and "WORD" (Microsoft Corp., Redmond, Wash.), both of which are available for "MACINTOSH" series computers (Apple Computer Corporation, Cupertino, Calif.), as well as IBM-compatible computers running "WINDOWS" (Microsoft Corp.).

IV. Therapeutic Applications

The results described herein may be used to develop εPKC-specific agents or compounds which, when given early in the course of impending infarction, may enhance the preconditioning response and thus reduce the morbidity and mortality in at-risk patients. Specifically, an εPKC-specific agonist peptide (e.g., peptide εV1-7) may itself be used therapeutically and/or used to develop a small molecule drug for the prevention of cardiac ischemia-induced damage. As opposed to agents which work more proximally in this signal transduction pathway, such an isozyme-selective agonist would have the advantage of being able to induce the preconditioning response in the myocardium without untoward side effects, such as negative inotropic effect, cardiac hypertrophy or arrhythmogenesis.

A. Therapeutic Peptides

The invention includes a method for reducing ischemic injury to a cell exposed to hypoxic conditions. In the method, a pharmaceutically-effective dose of a compound capable of activating εPKC (e.g., an εPKC-specific agonist peptide, such as peptide εV1-7) is delivered to the cardiac cells of a patient in need of treatment. Exemplary compounds include εPKC-specific agonist peptides such as peptides having sequences SEQ ID NO:6 or SEQ ID NO:7.

Several methods known in the art may be used to deliver the compound. In the case of peptides, an exemplary delivery method employs liposomes (e.g, fusogenic liposomes) loaded with the selected peptide using standard known methods. The liposomes may further be constructed to contain a targeting moiety or ligand, such as an antigen, an antibody, or a virus on their surface to facilitate delivery to the appropriate tissue (Betageri, et al., 1993). The liposomes are delivered to the heart by methods known in the art, for example, intracardiac injection or intracardiac catheter. The liposome preparation may be lyophilized for long-term storage according to methods known in the art.

In typical applications, the therapeutic compound is delivered to the cardiac cells at regular intervals for the duration of treatment, which is determined by the attending physician. For example, a therapeutic peptide may be delivered once to several times daily in bolus injections containing between about 1 and about 100 $\mu$g peptide. If the peptide is contained in an encapsulant (e.g., liposomes), the amount of the suspension delivered is adjusted so that the selected pharmaceutically-effective amount of peptide is delivered.

B. Gene Therapy

The invention also includes gene therapy methods and compositions suitable for reducing ischemic injury to a cell exposed to hypoxic conditions. In this aspect, a DNA sequence encoding an εPKC specific agonist peptide (e.g., peptide εV1-7) is cloned into a gene therapy vector effective to express the sequence in the tissue that is to be protected from ischemic injury. The construct thus formed is referred to as a chimeric polynucleotide or chimeric gene. The construct is useful in a method of reducing ischemic injury to a cell exposed to hypoxic conditions. In the method, the chimeric gene is introduced into the cell and expression of the DNA sequence encoding the εPKC agonist peptide is effective to reduce ischemic injury to the cell.

A number of gene therapy vectors are known to those skilled in the art. The vectors typically include a tissue-specific promoter operably linked to the coding sequence to control transcription of the coding sequence in the cell. The method may be applied to, for example, cardiac cells using a cardiac-specific promoter, kidney cells using a kidney-specific promoter, brain cells using a brain-specific promoter, and the like.

Molecular techniques and methods useful in the construction of expression vectors are well known in the art (e.g., Ausubel, et al., 1988; Sambrook, et al., 1989). The constructs can be tested by transfecting suitable animal models. Following transfection, the animals may be subjected to ischemic episodes and (optionally) reperfusion. The animals may then be sacrificed and the ischemic regions of the myocardium tested for the presence and extent of infarction as described, for example, by Thornton, et al. (1993), and for the presence of apoptosis as described, for example, in Gottlieb, et al. (1994). Sample biopsies may also be assayed for expression of the therapeutic peptide.

Any of a variety of methods known to those skilled in the art may be used to introduce gene therapy vectors of the present invention into selected target tissue cells. For example, gene therapy of cardiac tissue has included lipofection, retrovirus and adenovirus-mediated gene transfer, and injection of naked DNA directly into the vascular endothelium or cardiac tissue (Nabel, et al., 1990; Lin, et al., 1990; Leclere, et al., 1992; Flugelman, et al., 1990).

In viral-mediated gene transfer, host cells are transfected with nucleic acid constructs, containing fragments encoding an εPKC specific agonist peptide, by infection with mature virions containing hybrid vectors (the constructs along with selected viral sequences). The virions used to transfect host cells are preferably replication-defective, such that the virus is not able to replicate in the host cells.

The virions may be produced by co-infection of cultured host cells with a helper virus. Following coinfection, the virions are isolated (e.g., by cesium chloride centrifugation) and any remaining helper virus is inactivated. (e.g., by heating). The resulting mature virions contain a construct or chimeric gene of the present invention and may be used to infect host cells in the absence of helper virus. Alternatively, high titers of replication-defective recombinant virus, free of helper virus, may be produced in packaging cell lines containing those components for which the virus is defective (Miller, 1990).

Several types of viruses, including retroviruses, adeno-associated virus (AAV), herpes virus, vaccinia virus, and several RNA viruses may be amenable for use as vectors with chimeric gene or gene therapy constructs of the present invention. Each type of virus has specific advantages and disadvantages, which are appreciated by those of skill in the art. Methods for manipulating viral vectors are also known in the art (e.g., Grunhaus and Horowitz, 1992; Hertz and Gerard, 1993; and Rosenfeld, et al., 1991, 1992)

Retroviruses, like adeno-associated viruses, stably integrate their DNA into the chromosomal DNA of the target cell. Unlike adeno-associated viruses, however, retroviruses typically require replication of the target cells in order for proviral integration to occur. Accordingly, successful gene transfer with retroviral vectors depends on the ability to at least transiently induce proliferation of the target cells.

Retroviral vectors are attractive in part due to the efficiency of transfection—some vectors can stably transduce close to 100% of target cells. The use of retroviral vectors for in vivo gene therapy has been limited, in part, by the requirement of appropriate viral receptors on the target cell. Because the identities of most retroviral receptors are unknown, it has not been possible to determine the distribution of receptors in different cell types. Accordingly, the targeting of specific cell types by retroviral vectors has in many cases proven problematic.

This difficulty may be circumvented by modifying the envelope protein of the retrovirus to contain a ligand for a known endogenous (not necessarily viral) receptor expressed on the target cells. An application of this technique is described in detail by Kasahara, et al. (1994). Preferably, the virus also contains an unmodified envelope protein to facilitate cell entry. A number of receptors, such as desmin, E-selectin, and A-CAM, are expressed preferentially on cardiac cells and may be amenable to this approach (e.g., Hansen and Stawaski, 1994; Lefer, et al., 1994; Youker, et al., 1992).

Adeno-associated viruses are capable of efficiently infecting nondividing cells and expressing large amounts of gene product. Furthermore, the virus particle is relatively stable and amenable to purification and concentration. Replication-defective adenoviruses lacking portions of the E1 region of the viral genome may be propagated by growth in cells engineered to express the E1 genes (Jones and Shenk, 1979; Berkner, 1988; Graham and Prevea, 1991). Most of the currently-used adenovirus vectors carry deletions in the E1A–E1B and E3 regions of the viral genome. A number of preclinical studies using adenoviral vectors have demonstrated that the vectors are efficient at transforming significant fractions of cells in vivo, and that vector-mediated gene expression can persist for significant periods of time (Rosenfeld, et al., 1991, 1992; Quantin, et al., 1992; Stratford-Perricaudet, et al., 1992a; Rosenfeld, et al., 1991, 1992; Stratford-Perricaudet, et al., 1992b; Jaffe, et al., 1992). Several studies describe the effectiveness of adenovirus-mediated gene transfer to cardiac myocytes (Kass-Eisler, et al., 1993; Kirshenbaum, et al., 1993).

Herpes virus vectors (Breakefield and DeLuca, 1992; Freese, et al., 1990) are particularly well suited for the delivery and expression of foreign DNA in cells of the central nervous system (CNS), since they can efficiently infect mature, postmitotic neurons. Methods for manipulating the vectors and transfecting CNS cells are well known (see, e.g., Kennedy and Steiner, 1993; Yung, 1994). Studies utilizing direct injection of vectors into CNS tissue have been performed (e.g., Zhang, et al., 1992).

Another form of gene therapy vector delivery to cells in need of treatment is naked DNA injection. Plasmids bearing therapeutic constructs of the present invention may be purified and injected directly into a target tissue. Such approaches have been used successfully to express exogenous genes in rodent cardiac and skeletal muscle (Wolf, et al., 1990; Ascadi, et al., 1991a; Ascadi, et al., 1991b; Lin, et al., 1990; Kitsis, et al., 1991).

Still another route of DNA administration is via receptor-mediated gene transfer. Receptor-mediated endocytic pathways for the uptake of DNA may permit the targeted delivery of genes to specific cell types in vivo. Receptor-mediated methods of gene transfer involve the generation of complexes between plasmid DNA and specific polypeptide ligands (Wu, 1991) that can be recognized by receptors on the cell surface. One of the problems with receptor-mediated uptake for gene delivery is that the endocytic vesicles formed during this process may be transported to the lysosome, where the contents of the endosome are degraded. Methods have been developed to facilitate escape of the DNA from the endosome during the course of its transport. For example, either whole adenovirus (Wagner, et al., 1992a; Christiano, et al., 1993) or fusogenic peptides of the influenza HA gene product (Wagner, et al., 1992b) may be used to induce efficient disruption of DNA-containing endosomes.

In cases such as those outlined above, where a vector may be targeted to selectively transfect a specific population of cells, it will be understood that in addition to local administration (such as may be achieved by injection into the target tissue), the vector may be administered systemically (e.g., intravenously) in a biologically-compatible solution or pharmaceutically acceptable delivery vehicle. Vector constructs administered in this way may selectively infect the target tissue. The presence of a target tissue-specific promoter on the construct also provides an independent means of restricting expression of the therapeutic gene.

C. Advantages of Isozyme-Specific Therapeutic Compounds

Therapeutics designed in accordance with the invention effective to induce ischemic preconditioning have a number of advantages over presently-available compounds directed at inducing preconditioning via either non-specific PKC activation or by other means. With respect to the latter, although some preconditioning-inducing agents, such as adenosine agonists and endotoxins, are being developed (e.g., Baines, et al., 1996; Liu, G., et al., 1996, Khandoudi, et al., 1996), such agents typically exert only transient effects and appear to have undesirable side effects.

Similarly, the use of agents that non-specifically activate multiple PKC isozymes to achieve preconditioning poses several problems. First, whereas activation of some PKC isozymes may be beneficiary, activation of others may cause undesired side-effects. Such side effects may be manifested in the myocardium as deleterious effects on myocardial contractility, an increase in myocardial wall thickness, and an increased potential for arrhythmia. In addition, other organ toxicity may occur. For example, prolonged activation of PKC by phorbol esters (which induces preconditioning in vivo) can eventually lead to tumor promotion.

Second, it appears that for certain functions, specific PKC isozymes exert opposing effects. Specifically, in regulation of contraction rate, $\epsilon$PKC is very inhibitory whereas $\delta$PKC is slightly stimulatory (Johnson, et al., 1996). Therefore, if $\delta$PKC is deleterious to heart viability and $\epsilon$PKC is protective, only an $\epsilon$PKC-specific agonist will provide maximal protection.

Therefore, agents that selectively activate a PKC isozyme responsible for cardioprotective effects (i.e., $\epsilon$PKC) offer distinct advantages as therapeutics for ischemia-induced damage, over both non-selective PKC activators and PKC-independent preconditioning-inducing agents.

V. Screening Applications

Isozyme-specific agonist peptides, such as peptide $\epsilon$V1-7 (SEQ ID NO:6), may be used in conjunction with their corresponding isozyme PKC (e.g., $\epsilon$PKC) in a screen to identify compounds effective to competitively displace the peptide from PKC or to prevent the peptide from binding to PKC. Such compounds would be expected to act as PKC agonists, and could be tested further, e.g., as described herein, for isozyme specificity, ability to induce preconditioning, and the like.

In one example of such a screening method, $\epsilon$PKC is immobilized inside the wells of a multiwell plate (e.g., 96-well plate) by introducing a solution containing the PKC into the plate and allowing the PKC to bind to the plastic. The wells may be precoated with substance(s) that enhance attachment of the PKC to be immobilized and/or decrease the level of non-specific binding.

The plate is then incubated with a blocking solution (containing, for example, bovine serum albumin (BSA)) and then washed several times. A solution containing reporter-labelled (e.g., radiolabelled of fluorescently-tagged) peptide $\epsilon$V1-7 (SEQ ID NO:6) and, in the case of experimental (vs. control) wells, a test compound is added. Different wells may contain different test compounds or different concentrations of the same test compound. Each test compound at each concentration is typically run in duplicate and each assay is typically run with negative (wells with no test compound) as well as positive (wells where the "test compound" is, e.g., unlabeled peptide) controls. The free peptide is then washed out, and the degree of binding in the wells assessed.

A test compound is identified as active if it significantly decreases the binding of the peptide, i.e., if its effect on the extent of binding is above a threshold level (e.g., a several-fold difference in binding level between control and experimental samples). In one embodiment, the threshold is a 2-fold difference. In another embodiment, it is a 5-fold difference. In yet another it is a 10-fold or greater difference.

It will be appreciated that the test compound can alternatively be added after the wells had been incubated with labelled peptide, and the wells monitored for a decrease in bound peptide in the presence of the compound.

Detection methods useful in such assays include antibody-based methods (i.e., an antibody directed against the peptide), direct detection of a reporter moiety incorporated into the peptide (such as a fluorescent label), and proximity energy transfer methods (such as a radiolabeled peptide resulting in fluorescence or scintillation of molecules incorporated into the immobilized PKC or the solid support).

In particular, multiwell plates (e.g., 96-well plates) that contain a scintillating material in the wells (available from, e.g., Wallac, Gaithersburg, Md.) may be coated with a selected isozyme of PKC and used in conjunction with radioactively-labeled isozyme-specific agonist peptide. Peptide that binds the immobilized PKC is constrained within a few nanometers of the well surface, resulting in light emission from the scintillation material in the wells. The signal can be quantitated using a plate reader or counter, such as the "MICROBETA PLUS" plate counter (Wallac, Gaithersburg, Md.), to generate standard binding plots.

A variety of different test compounds may be screened using methods of the present invention. They include peptides, macromolecules, small molecules, chemical and/or biological mixtures, and fungal, bacterial, or algal extracts. Such compounds, or molecules, may be either biological, synthetic organic, or even inorganic compounds, and may be obtained from a number of sources, including pharmaceutical companies and specialty suppliers of libraries (e.g., combinatorial libraries) of compounds.

Methods of the present invention are well suited for screening libraries of compounds in multi-well plates (e.g., 96-well plates), with a different test compound in each well. In particular, the methods may be employed with combinatorial libraries. A number of small-molecule libraries have been developed (e.g., Bunin, et al., 1994; Bunin and Ellman, 1992; Virgilio and Ellman, 1994).

VI. Drug Lead Applications

An $\epsilon$PKC selective agonist peptide (e.g., peptide $\epsilon$V1-7) can be translated into a bioavailable low molecular weight organic drug lead compound that mimics preconditioning and reduces ischemia induced cardiac muscle damage. This compound can then be tested for its ability to induce protection of cardiac muscle from prolonged ischemia in cardiomyocytes in culture, in isolated heart preparations and in vivo in intact animals, e.g., as described herein.

The steps typically performed in translating a peptide into a peptide mimetic (e.g., a small organic compound) with similar bioactivity are known (see, e.g., Moore, 1994). The steps can be summarized as follows:

Step 1—Identification of the pharmacophoric groups that are responsible for agonist activity through structure-function analyses. An example of such an analysis is the "alanine scanning" analysis (e.g., Beck-Sickinger and Jung, 1995; Goldberg, et al., 1993; Nagashima, et al., 1993), which can be used to identify the side chains that are required for the $\epsilon$PKC-agonist effects of peptide $\epsilon$V1-7.

Step 2—Physical structure analysis of "active" peptide sequences identified in Step 1 with a recombinant target protein to determine the structural relationship of the bound peptides to the target. This can be done using, e.g., NMR spectroscopy or X-ray crystallography, and the spectroscopic or crystal structure can be refined (e.g., subjected to energy minimization algorithms) using a computer. Conveniently, the crystal and NMR structures of the RACK binding site of $\beta$PKC are now available for such analyses (Shao, et al., 1996).

Step 3—Constructing a template (formed of organic molecule building blocks, such as benzene, phenanthrane, benzodiazapine, alkyl chains, etc.) onto which pharmacophoric groups can be mounted in a manner that allows them to retain the spatial relationships established in Step 2.

Step 4—Apply in vitro high throughput screening assays of libraries of molecules based on the template(s) designed in Step 3. The assays described herein, particularly the agonist peptide displacement assay, can be employed in such high throughput screens.

It will be understood that various modifications to the above steps can be made by one of skill in the art without departing from the invention.

Potential PKC-activating compounds (such as the compounds developed as designed above) may then be tested in any of a number of in vitro and/or in vivo assays. Typically, such compounds would initially be tested for effects in cell-based assays, such as the cell viability assays described herein. The compounds may also be tested using isolated heart preparations (e.g., Mitchell, et al., 1993, 1995) to determine ischemia-induced cell damage and protection by preconditioning. Suitable animal models, e.g., rat or mouse models (e.g., Link, et al., 1996), may be used to test the compounds in vivo. The animal studies may be used to determine (i) the effects of different routes of administration (intracoronary, i.v., s.c., p.o., etc.), (ii) dose-tissue responses, and (iii) any possible side effects (e.g. negative inotropic effect of alteration of automaticity threshold). In vivo studies can also be used to measure drug effects on standard cardiovascular parameters such as heart rate and blood pressure, as well as for dose-tissue responses. Additional studies may be performed to optimize the route of administration (especially for intracoronary administration) on cardiac function and response to ischemia induced by coronary artery occlusion and during cardio-pulmonary bypass with aortic cross-clamping, and to determine optimal dosage. Dosages can then be incorporated to humans or other large species, according to estimations and procedures that are standard in the art. Wall motion abnormalities may be assessed and cardiac contractility may be measured using the end-systolic pressure volume relationship with ventricular volumes derived real-time via the conductance catheter method.

VII. Utility

The present invention has applications in treatment of surviving heart attack victims as well as those who presently die from heart disease after admission to the hospital. As stated above, it is now recognized that angina is a natural form of preconditioning: patients who have a history of angina fare better after a myocardial infarction event than those who have never had angina (Kloner and Yellon, 1994; Kloner, et al., 1995). An εPKC selective agent could be valuable in the management of these patients, both acutely and chronically.

Acutely, in patients brought to hospital with impending infarction, medical care has been directed towards removing the cause of coronary occlusion either by thrombolytics or by catheter angioplasty. However, reperfusion of the damaged areas can be one of the major mechanisms of myocardial cellular injury. An εPKC selective agent could be delivered to the site of occlusion by catheter or be injected intravenously to induce cardioprotection immediately before or concurrently with thrombolysis or angioplasty.

Chronically, in patients with angina, the current medical approach is to stop the symptoms of angina without replacement of angina's preconditioning protective effect. An injectable or orally available εPKC selective agonist could be used to replace the preconditioning effect induced by angina in these patients and offer a higher rate of myocardial salvage during future episodes of more severe ischemia.

Additional uses of the invention include clinical situations in which the timing of ischemia is physician-controlled. In such instances, pharmacologic enhancement of the preconditioning response would provide a significant advantage to the patients undergoing treatment. Specifically, each year, in the United States alone, 600,000 adults and 12,000 children undergo open heart operations utilizing cardiopulmonary bypass, during which the heart is subjected to periods of controlled ischemia ranging from several minutes to well over one hour. Despite advances in cardiac protection, myocardial dysfunction during the immediate post-operative period remains a leading cause of morbidity and mortality in these patients. Because the exact timing of the ischemic insult is known ahead of time in these patients, treatments in accordance with the invention could significantly reduce myocardial damage by inducing a preconditioning response in the hours or days prior to surgery.

Similar benefits could be realized in the area of cardiac transplantation, of which there are approximately 2500 cases annually in the U.S. Prolonged graft ischemia is one of the factors limiting long-distance donor organ acquisition for such cardiac transplantation. Administration of an εPKC agonist at the time of organ procurement could extend the time between organ harvest and implantation and reduce the risk of post-operative myocardial dysfunction.

It will, of course, be understood that the present invention may employed in the treatment of a variety of ischemic and hypoxic conditions, in addition to cardiac ischemia. For example, methods and compositions of the invention may be applied to the treatment of ischemia-induced damage in the kidney, in the vascular endothelium, and in the central nervous system (e.g., to damage caused by stroke).

The following examples illustrate but in no way are intended to limit the present invention.

MATERIALS AND METHODS

Unless otherwise indicated, phorbol esters were purchased from LC Laboratories (Woburn, Mass.), monoclonal anti-human Hsp70 antibody was purchased from StressGen Biotechnologies (Sidney, BC, Canada), and all other reagents were purchased from Sigma Chemical Company (St. Louis, Mo.).

A. Peptides

Peptides were synthesized at the Beckman Center Protein and Nucleic Acid Facility at Stanford University (Stanford, Calif.). The peptides were typically greater that 90% pure.

Abbreviations used below include the following. PAGE: polyacrylamide gel electrophoresis; SDS: sodium dodecyl sulfate; BSA: bovine serum albumin.

B. Buffers

Phosphate-buffered saline (PBS)

10× stock solution, 1 liter:
80 g NaCl
2 g KCl
11.5 g $Na_2HPO4$—$7H_2O$
2 g $KH_2PO_4$ Working solution, pH 7.3:
137 mM NaCl
2.7 mM KCl
4.3 mM $Na_2HPO_{4-7}H_2O$
1.4 mM $KH_2PO_4$ C. Ventricular Myocyte Preparation Primary cell cultures were prepared as previously described (Disatnik, et al., 1994). Briefly, ventricles from day-old Sprague-Dawley rats were minced, and single isolated myocytes were obtained by alternating cycles of room temperature trypsinization and mechanical dissociation. Cells were washed and preplated in medium 199 with Hanks' salt solution (Gibco/BRL Life Technologies, Gaithersburg, Md.) containing 10% fetal bovine serum (Hyclone Laboratories, Inc., Logan, Utah) to reduce the number of contaminating non-myocardial cells (NMCs). After 30 minutes nonattached cardiac myocytes were collected and replated at a density of 800 cells per $mm^2$ into 8-well glass chamber slides (Nunc, Naperville, Ill.) for cell viability assays and immunofluorescence staining, into 6-well plastic culture plates (Fisher Scientific, Pittsburgh, Pa.) for lactate dehydrogenase (LDH) assays, or into 100 mm glass culture dishes for Western blot analyses. Myocytes were maintained in medium 199 (M-199) supplemented with 1.5 mM vitamin $B_{12}$, 50 U/ml penicillin, 80 mM vitamin C, and 10% fetal bovine serum. During this period, the medium also contained 0.1 mM bromodeoxyuridine to prevent the proliferation of any remaining NMCs (Simpson, et al., 1982). Cells were then placed in defined medium on culture day 4 consisting of M-199 supplemented with 1.5 mM vitamin $B_{12}$, 50 U/ml penicillin, 80 mM vitamin C, 10 mg/ml insulin, and 10 mg/ml transferrin. The resulting cell preparation contained 90–95% cardiac myocytes. Cell numbers remained constant for at least 8 days. Experiments were conducted on culture days 6–8.

D. Induction of Hypoxia

Both hypoxic preconditioning and prolonged hypoxic challenges were carried out by transferring cultured cardiac myocytes into and out of a sealed plexiglass chamber (Anaerobic Systems, San Jose, Calif.) maintained at 37° C. with a humidified atmosphere of 1% $CO_2$, less than 0.5% $O_2$, with the balance $N_2$. Routine monitoring with a Fyrite Gas Analyzer (Bacharach Instruments, Pittsburgh, Pa.) verified that oxygen concentrations remained between 0.2% and 0.5%. Normoxic incubations of cultured myocytes were conducted in a Forma Scientific water-jacketed incubator gassed with 99% air and 1% $CO_2$ at 37° C.

In initial experiments, hypoxic preconditioning consisted of four 90 minute periods of hypoxia alternating with 60 minute incubations under normoxic conditions. Cardiac myocytes were kept in their original glucose-supplemented (5 mM glucose) defined culture media throughout the multiple-cycle preconditioning protocols. In later single-cycle hypoxic preconditioning experiments, myocytes were fed with fresh, pre-equilibrated, glucose-free defined culture media within the hypoxia chamber for 30 minutes. For phorbol ester preconditioning experiments, myocytes were stimulated with 10 nM 4β-phorbol 12-myristate 13-acetate (PMA) for 10 minutes then washed with fresh defined media.

Cultured cardiac myocytes were subjected to a prolonged hypoxic challenge by transferring them into the plexiglass chamber, where they were fed with fresh, glucose-free defined culture media that had been pre-equilibrated for several hours within the hypoxic environment. Cells were removed 7–9 hours later and immediately underwent the indicated analyses. Previous experiments demonstrated that 2 hours of hypoxia resulted in a medium $PO_2$ of 23.9±1.5 Torr, pH of 7.34±0.02, and $pCO_2$ of 46.6±0.7 Torr. LDH release from glucose-supplemented myocytes subjected to 2 hours of hypoxia and from glucose-deprived myocytes subjected to 30 or 60 minutes of hypoxia was no different from that of normoxic control cells. These data support the view that preconditioning itself does not cause irreversible cellular damage.

E. Western Blot Analysis

Western blot analyses of cardiac myocytes grown on 100 mm glass dishes were carried out as previously described (Liu, Y., et al., 1995). Following treatment, medium from one plate was removed, and cells were washed twice with ice-cold phosphate-buffered saline (PBS). 1.5 ml of chilled homogenization buffer consisting of 10 mM Tris-HCl pH 7.4, 1 mM EDTA, 1 mM EGTA, 0.25 M sucrose, and 20 mg/ml each of phenylmethylsulfonyl fluoride, soybean trypsin inhibitor, leupeptin, and aprotinin was added to each dish. Myocytes were scraped from the plates and triturated 3 times with a tuberculin syringe attached to a 22-gauge needle. The resulting lysates were centrifuged at 4° C. for 30 minutes at 100,000× g in a Beckman Ti 100.3 rotor (Beckman Instruments, Columbia, Md.). Supernatants were concentrated to a volume of 250 ml with a Centricon 30 filtration unit (Amicon, Beverly, Mass.). Pellets were resuspended in 250 ml of homogenization buffer with a tuberculin syringe attached to a 22-gauge needle. Soluble and particulate fractions were then subjected to 12% SDS-PAGE and transferred to nitrocellulose sheets. βPKC levels were determined using monoclonal anti-βPKC antibodies (Seikagaku Kogyo, Tokyo, Japan) diluted 1:1000 followed by incubation with rabbit anti-mouse IgG antibodies (Cappel, Durham, N.C.), also at 1:1000 dilution. δPKC and εPKC levels were determined using rabbit polyclonal anti-δPKC and anti-εPKC antibodies (Gibco/BRL), each at 1:300 dilution. Western blots were then incubated with $^{125}$I-protein A (ICN Biomedicals, Inc., Irvine, Calif.), and PKC immunoreactive bands were detected by autoradiography.

F. Cell Viability Assay

Following treatment of cardiac myocytes grown on 8-well chamber slides, living and dead cells were distinguished using the "EUKOLIGHT" Viability/Cytotoxicity assay (Molecular Probes, Eugene, Oreg.). Culture medium was aspirated from each well and replaced for 30 minutes with 2 mM calcine acetoxymethyl ester and 4 mM ethidium homodimer-1 diluted in medium 199. Slides were then viewed with a Zeiss IM35 microscope using a 40X water immersion objective. The number of viable (green fluorescent by calcine) and non-viable (red fluorescent by ethidium) cardiac myocytes present in 10–20 random microscopic fields per condition per experiment was recorded.

G. Immunofluorescence Staining

Immunofluorescence staining of cardiac myocytes grown on 8-well glass chamber slides was carried out as previously described (Hauser, et al., 1993). Following each treatment culture medium was removed, and cells were washed twice with ice-cold PBS. Myocytes were fixed for 3 minutes with cold methanol and acetone, then washed twice more with PBS. Non-specific binding was blocked by pre-incubating cells for 1 hour at room temperature with 1% normal goat serum (NGS; Cappel, Durham, N.C.) in PBS with 0.1% Triton X-100 (NGS/PBS/Triton). Cells were then incubated for 4 hours at room temperature with isozyme-specific rabbit polyclonal antibodies (R&D Antibodies, Minneapolis, Minn.) directed against $β_I$PKC, δPKC, or εPKC diluted 1:100 in PBS/Triton with 2 mg/ml BSA. Myocytes were washed 3 times with PBS/Triton and then incubated for 2 hours at room temperature with FITC-conjugated goat anti-rabbit IgG antibodies diluted 1:1000 in NGS/PBS/Triton. Cells were then washed 3 times with PBS/Triton, 2 times with deionized water, and allowed to air dry. Following mounting of glass coverslips with "VECTASHIELD" medium (Vector Laboratories, Burlingame, Calif.), slides were viewed with a Zeiss IM35 microscope using a 40× water immersion objective. Images were recorded on Kodak TMAX 400 film with exposure time of 1 second for all photomicrographs and were processed by an automated, commercial developer without additional adjustment.

H. Lactate Dehydrogenase Assay

The effect of hypoxia on cellular LDH release from cardiac myocytes grown in 6-well plastic plates was assessed as previously described (Rocha-Singh, et al., 1991). Following each treatment, culture media were removed, vortexed, and stored at 4° C. To recover the LDH activity retained by surviving cardiac myocytes, an equal volume of cold lysing buffer consisting of 10 mM Tris-HCl pH 7.4 and 1 mM EDTA was added to each well. Myocytes were scraped and triturated 3 times with a tuberculin syringe attached to a 22-gauge needle. The resulting lysates were centrifuged at 4° C. for 15 minutes at 50,000× g. 100 ml aliquots from culture media samples (released LDH) and from supernatants of cell lysates (retained LDH) were then analyzed using a commercially available assay in which the rate of decrease in absorbance of the sample at 340 nm is directly proportional to LDH activity (Sigma Diagnostics, St. Louis, Mo.). LDH activity was expressed as units per liter (U/L), where one unit is defined as the amount of enzyme catalyzing the formation of 1 mmol/L of NAD per minute under the conditions of the assay.

I. Transient Permeabilization of Cardiac Myocytes

Transient permeabilization of cardiac myocytes grown on 8-well glass chamber slides or on 100 mm glass culture dishes was carried out with saponin (50 μg/ml). Immediately prior to each treatment, conditioned medium from each culture vessel was removed and set aside at 37° C. Myocyte temperature was lowered gradually to 4° C. with serial PBS washes. Cells were then incubated for 10 minutes with chilled permeabilization buffer consisting of 10 mM EGTA, 140 mM KCl, 20 mM HEPES pH 7.4, 50 mg/ml saponin, 10 mM $K_2$oxalate, and 6 mM ATP with or without 10 mM PKC-derived peptide of interest. Permeabilization buffer was then aspirated, and myocytes were washed several times with cold PBS prior to a 20 minute recovery period on ice. Cell temperature was raised gradually to 37° C. with serial PBS washes The previously set aside, warm conditioned medium was then returned to each culture vessel, and myocytes were allowed to recover an additional 15–30 minutes at 37° C. prior to the onset of each experiment. Transient saponin permeabilization carried out according to this protocol did not alter cardiac myocyte viability, spontaneous or stimulated contraction rates, basal or hormone-induced expression of c-fos mRNA, or growth factor-induced hypertrophy.

J. Statistical Analysis

Data were expressed as mean±SEM. Numerical data were compared using Student's t test for paired observations between two groups and by ANOVA followed by the Bonferroni t test when more than two groups were analyzed. A P value of <0.05 was considered significant.

EXAMPLE 1

Cardiac Myocyte Hypoxia Preconditioning

Cardiac myocytes were subjected to preconditioning as described above. The initial preconditioning paradigm consisted of four 90 minute periods of hypoxia alternating with 60 minute incubations under normoxic conditions. The duration of each hypoxic period was chosen based on the observation that cultured myocytes incubated under hypoxic conditions in glucose-supplemented media for up to 2 hours demonstrated no reduction in viability. The number of cycles was chosen based on data from a study of ischemic preconditioning in canine myocardium (Murry, et al., 1986), in which 4 brief coronary artery occlusions protected cardiac tissue from a subsequent prolonged period of ischemia (Murry, et al., 1986). The potential protective effect of the preconditioning protocol against hypoxia-induced irreversible damage was determined using a fluorescence-based cell viability assay that discriminated between living and dead myocytes upon completion of the prolonged hypoxic challenge. This method has been validated with a variety of adherent cell types (Hauser, et al., 1993) as well as with primary cultures of neonatal rat cardiac myocytes (Kirshenbaum and Schneider, 1994).

Figure 1B:
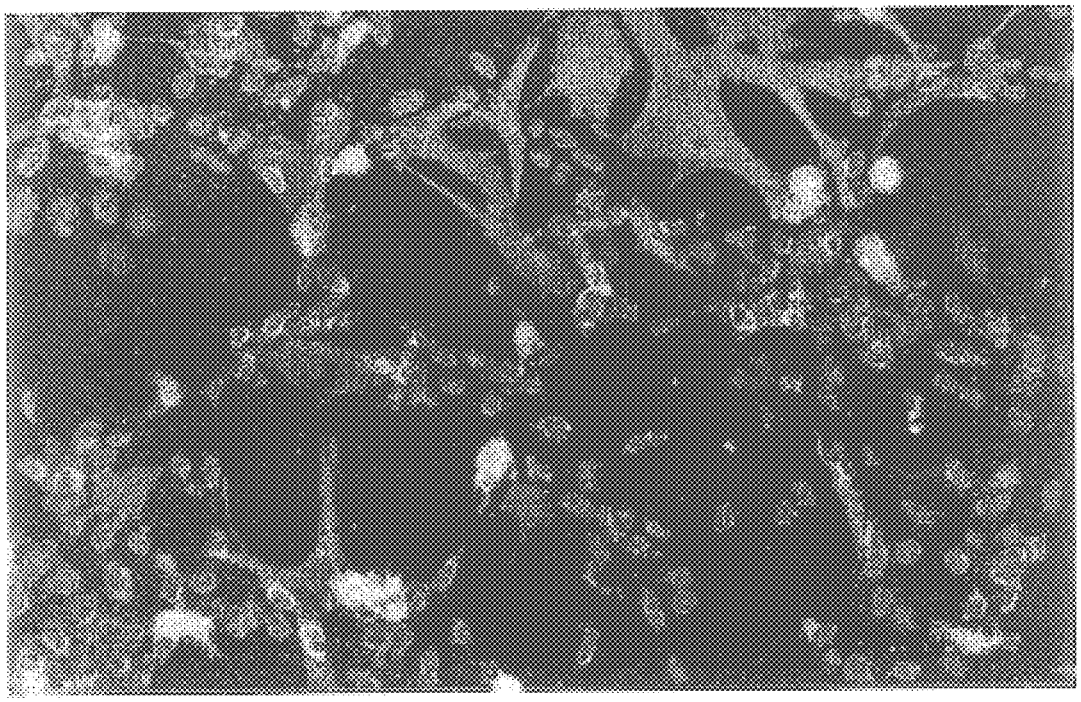

Cultured myocytes were labeled with 2 mM calcine acetoxymethyl ester and 4 mM ethidium homodimer-1 and then scored as either viable (green fluorescent by calcine) or non-viable (red fluorescent by ethidium). FIG. 1A shows results of myocytes maintained under normoxic conditions. FIG. 1B shows results of myocytes following 9 hours of hypoxia.

It can be appreciated from FIGS. 1A and 1B that the proportion of viable cardiac myocytes in cultures maintained under normoxic conditions was consistently greater than 95% (FIG. 1A). In contrast, in cells were transferred to the hypoxia chamber, the proportion of non-viable cardiac myocytes increased and exceeded 50% after 7–9 hours of exposure to 0% oxygen (FIG. 1B).

The hypoxic preconditioning itself had no immediate effect on cardiac myocyte survival. In 2 independent experiments, a total of 20 random microscopic fields per condition (600 cells each) were scored just after the final preconditioning cycle. The proportion of viable cells in the preconditioned group was 96.5±0.7% versus 97.2±0.8% for normoxic control myocytes (P=NS).

Figure 2A:
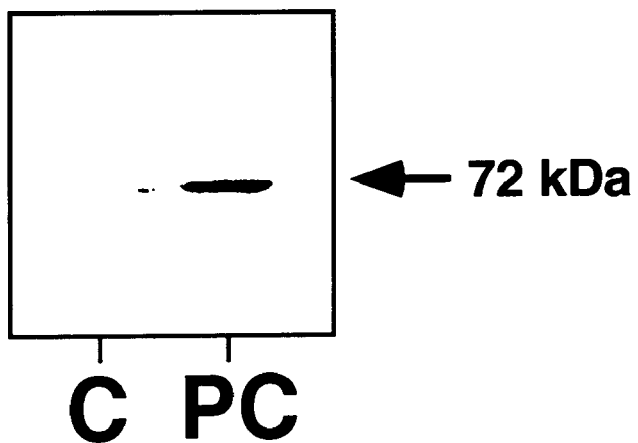
FIG. 2A shows the effects of hypoxic preconditioning on the expression of the inducible 72 kDa member of the heat shock protein 70 kDa family (Hsp70) in cardiac myocytes.
Figure 2B:
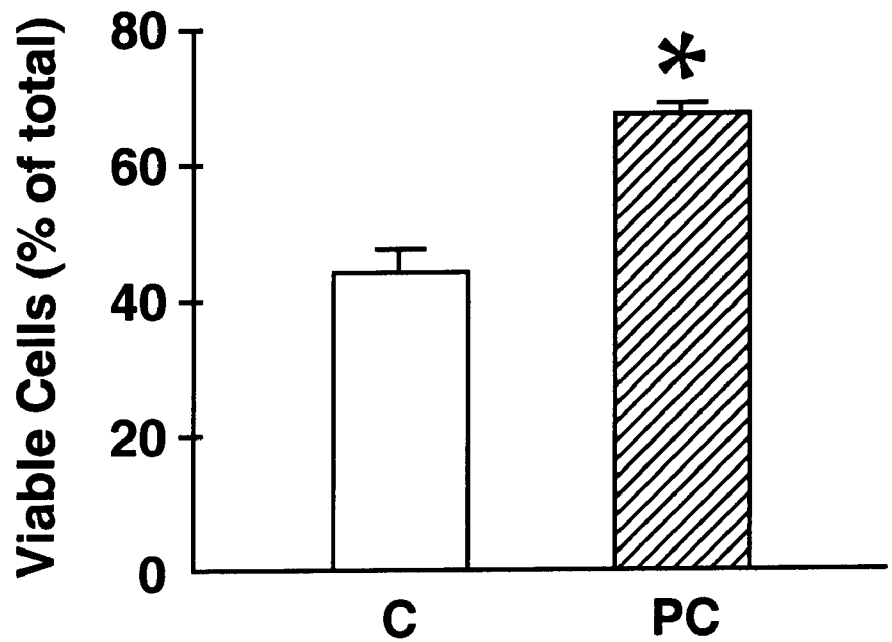
FIG. 2B shows the effects of hypoxic preconditioning on myocyte viability.
Figures 3A, 3B, 3C:
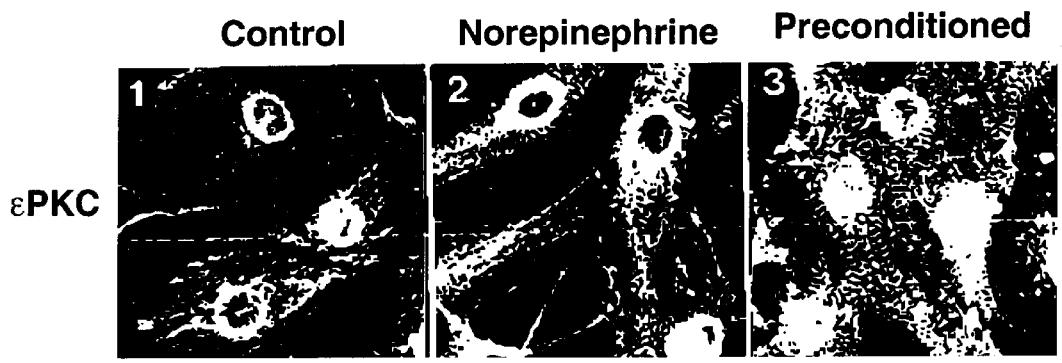
FIGS. 3A–3F show immunohistochemical detection of εPKC (FIGS. 3A, 3B and 3C) and εPKC (FIGS. 3D, 3E and 3F) in control, norepinephrine-stimulated and preconditioned cardiac myocytes.
Figures 3D, 3E, 3F:
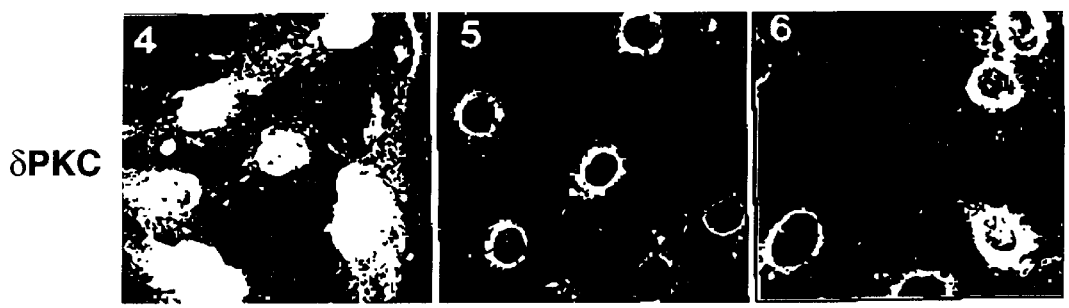

The hypoxic preconditioning did, however, have a strong positive effect on the expression of the inducible 72 kDa member of the heat shock protein 70 kDa family (Hsp70). Cardiac myocytes underwent preconditioning with four 90 minute periods of hypoxia alternating with 60 minute normoxic incubations. Lysates of the preconditioned and control cells were analyzed by Western Blot using anti-Hsp70 antibodies as described above. Exemplary results are shown in FIG. 2A. In control cardiac myocytes (C), Hsp70 was barely detectable, whereas hypoxic preconditioning (PC) upregulated the expression of Hsp70 protein by several fold. The data are representative of two independent experiments.

The effect of preconditioning on myocyte viability was determined by subjecting preconditioned and control myocytes to 9 hours of hypoxia followed by determination of cell viability. 20 random fields per condition in each of 4 independent experiments were scored. The results are shown in FIG. 2E. Myocytes that had undergone 4 cycles of hypoxic preconditioning are indicated by "PC" and control myocytes are indicated by (C).

As can be appreciated from the data, preconditioning increased the proportion of surviving myocytes by 52% compared with control (66.5±1.4% versus 43.7±3.3%). The number in each bar represents the total number of cells scored per condition. *P<0.01 versus control. These results validate this assay as a cardiac myocyte culture model for hypoxic preconditioning.

EXAMPLE 2

Hypoxic Preconditioning Results in Selective Activation of $\delta$ and $\epsilon$PKC Isozymes To determine whether hypoxic condition results in selective upregulation of any PKC isozymes, myocytes were exposed to 4 cycles of hypoxic preconditioning or were stimulated with 2 mM norepinephrine for 2 minutes under normoxic conditions, and were then fixed and stained with antibodies to $\epsilon$PKC, $\delta$PKC or $\beta_I$PKC.

Exemplary results are shown in FIGS. 3A–3F. The cells in FIGS. 3A, 3B and 3C were stained with antibodies to $\epsilon$PKC, while cells in FIGS. 3D, 3E and 3F were stained with antibodies to $\delta$PKC. As can be appreciated from the data, hypoxic preconditioning resulted in selective activation of $\delta$ and $\epsilon$PKC isozymes.

Figures 4A, 4B, 4C:
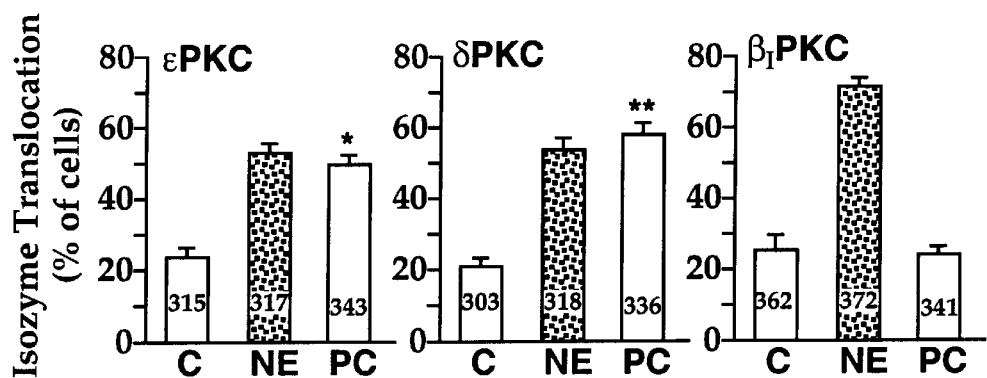
FIGS. 4A, 4B and 4C are computer-generated images that show the degree of PKC stimulation in cardiac myocytes for different PKC isoforms in response to norepinephrine stimulation and preconditioning.

Myocytes displaying activated $\epsilon$PKC (cross-striated staining), $\delta$PKC (perinuclear staining), or $\beta_I$PKC (intranuclear staining) in 15 random fields per condition per PKC isozyme in 2 independent experiments were scored. The results are summarized in FIGS. 4A ($\epsilon$PKC), 4B ($\delta$PKC) and 4C ($\beta_I$PKC). Preconditioning (PC) produced a 2.1 fold increase in $\epsilon$PKC activation and a 2.8 fold increase in $\delta$PKC activation over control (C). No activation of $\beta_I$PKC by hypoxic preconditioning was observed. For comparison, activation of these isozymes by 2 mM norepinephrine (NE) was also determined. The number in each bar represents the total number of cells scored per condition. *P<0.05 versus control. **P<0.05 versus control.

EXAMPLE 3

Selective Activation of PKC Isozymes by Short Exposure to 10 nm PMA

The ability of PMA to activate the PKC isozymes $\alpha$PKC, $\beta$PKC, $\delta$PKC and $\epsilon$PKC was evaluated. Exemplary results are shown in FIGS. 5A, 5B, 5C and 5D, respectively, each of which shows a Western Blot of cardiac myocyte soluble and particulate fractions run individually in three lanes and detected with anti-PKC antibodies as described above. Myocytes were incubated with 10 nM PMA for 10 minutes then harvested either immediately (lane 2) or washed with fresh medium and harvested 12 hours later (lane 3). Lane 1 shows results for controls (no PMA incubation).

The analyses revealed no translocation of $\alpha$PKC and minimal translocation of $\beta$PKC from the cell soluble to the cell particulate fraction. In contrast, translocation of $\delta$PKC and $\epsilon$PKC in response to PMA was robust. Twelve hours after PMA stimulation (lane 3), the amount and distribution of PKC isozymes in the two cell fractions was indistinguishable from that of control cells (lane 1). Results are representative of two independent experiments.

EXAMPLE 4

Activation of εPKC is Required for PMA- and Preconditioning-Induced Protection of Cardiac Myocytes from Subsequent Prolonged Hypoxia Studies were conducted to determine of activation of εPKC is required for PMA- and preconditioning-induced protection of cardiac myocytes from subsequent prolonged hypoxia. εPKC specificity was assayed using the εPKC-selective peptide inhibitor εV1-2 (SEQ ID NO:3). Myocytes were permeabilized to introduce peptide εV1-2 (SEQ ID NO:3), control peptide εV1-3 (SEQ ID NO:4), or no peptide (——). Cells were then stimulated with 10 nM PMA for 10 minutes (Phorbol Ester) or vehicle (Control), washed, and subjected to 9 hours of hypoxia. 10 random fields per condition in each of 4 independent experiments were scored for cell viability.

The results for PMA-induced protection are shown in FIG. 6A. Exposure to PMA increased the proportion of surviving myocytes by 34% versus control. Protection was abolished by the εPKC-selective antagonist peptide εV1-2 (SEQ ID NO:3). The number in each bar represents the total number of cells scored per condition. ↑$P<0.05$ versus control cells. *$P<0.05$ versus PMA-treated cells permeabilized in the absence of peptide (——) or in the presence of εPKC-derived control peptide (εV1-3).

Figure 6C:
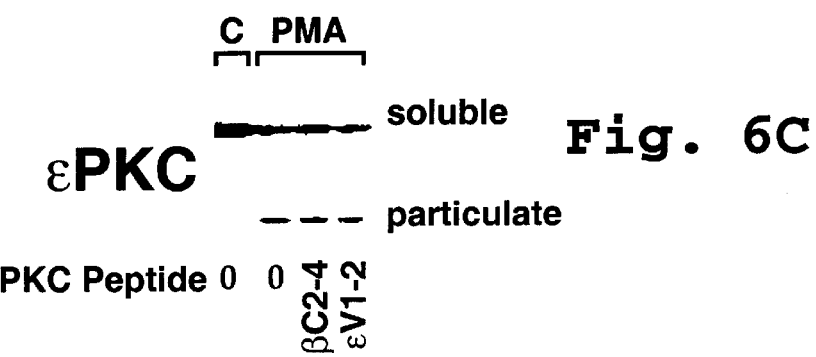
FIGS. 6C and 6D show the effect of isoform-specific inhibitory peptides on PMA- (FIG. 6C) or preconditioning- (FIG. 6D) induced PKC translocation.

A similar experiment was conducted to determine the effect of isoform-specific inhibitory peptides on PMA-induced PKC translocation. The results are shown in FIG. 6C. Myocytes were permeabilized to introduce peptide εV1-2 (SEQ ID NO:3), peptide βC2-4 (SEQ ID NO:1; a βPKC-selective antagonist peptide), or no peptide (0) and then stimulated with 10 nM PMA for 10 minutes (PMA) or with vehicle (lane labeled C). Western blot analysis of control and treated cell soluble and particulate fractions revealed inhibition of PMA-induced εPKC translocation only in the presence of the εPKC-selective peptide antagonist εV1-2 (SEQ ID NO:3). Densitometry of the original autoradiogram revealed a 23% reduction in the particulate signal in the lane labeled εV1-2 compared with PMA alone. Result is representative of two independent experiments.

The results for hypoxia preconditioning-induced protection as assayed by cell viability are shown in FIG. 6B. Myocytes were permeabilized to introduce εV1-2 (SEQ ID NO:3), control peptide βC2-4 (SEQ ID NO:1), or no peptide (——) and then exposed to 30 minutes of hypoxia in the absence of glucose (Preconditioned). After 30 minutes of recovery under normoxic conditions, preconditioned and control cells were subjected to 9 hours of hypoxia. 20 random fields in each of 2 independent experiments were scored for cell viability. Preconditioning increased the proportion of surviving cells by 86% versus control. Protection was abolished by peptide εV1-2 (SEQ ID NO:3). The number in each bar represents the total number of cells scored per condition. ↑↑$P<0.05$ versus control cells. **$P<0.05$ versus preconditioned cells permeabilized in the absence of peptide (——) or in the presence of control peptide ηC2-4 (SEQ ID NO:1).

Figure 6D:
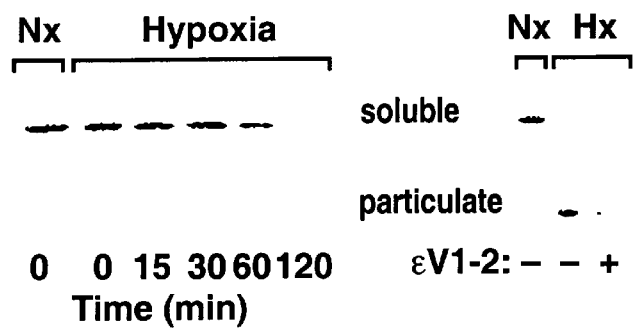

The effects of isoform-specific inhibitory peptides on hypoxia preconditioning-induced PKC translocation are shown in the left panel of FIG. 6D. Myocytes were either maintained in glucose-supplemented medium under normoxic conditions (Nx) or incubated in glucose-free medium under hypoxic conditions (Hypoxia) for the times indicated. Western blot analysis revealed translocation of εPKC from the soluble to the particulate fraction following 30–120 minutes of hypoxia. Result is representative of two independent experiments.

The right panel of FIG. 6D shows a Western analysis of myocytes maintained in glucose-free medium and permeabilized in the presence of εV1-2 (+) or in the absence of peptide (——) and then either incubated under normoxic conditions (Nx) or exposed to 1 hour of hypoxia (Hx). It can be appreciated that hypoxia induced translocation of εPKC from the soluble to the particulate fraction that was inhibited by the εPKC-selective peptide antagonist εV1-2 (SEQ ID NO:3). Result is representative of two independent experiments.

EXAMPLE 5

Peptide Activation of PKC Assayed by Substrate Phosphorylation

Activation of εPKC by peptide εV1-7 (SEQ ID NO:6) was measured by phosphorylation of one of its substrates, calsequestrin. The εV1-7 peptide (10 mM) was incubated with εPKC (~10 nM) for 15 minutes at room temperature in overlay buffer (50 mM Tris-HCl pH 7.5 containing 0.1% bovine serum albumin (BSA), 5 mg/ml leupeptin, 10 mg/ml soybean trypsin inhibitor (SBTI), 0.1% polyethylene glycol (PEG), 0.2M NaCl, 0.1 mM $CaCl_2$ and 12 mM β-mercaptoethanol). Calsequestrin (0.2 mg/ml) was then added to the mixture along with 20 mM Tris-HCl pH 7.5 containing $MgCl_2$ (20 mM), β-meracptoethanol (12 mM), ATP (20 mM) and [$\gamma$-$^{32}$P]ATP (5 mCi/ml). In some experiments (indicated), the PKC activators DG (1.2 μg/ml) and/or PS (50 μg/ml) were also added. The mixture was incubated for 15 minutes at room temperature and the reaction stopped by addition of sample buffer. The samples were then boiled for 10 minutes and loaded onto 10% SDS-PAGE minigel. The gel was fixed with 50% methanol and 10% acetic acid for 1 hour and calsequestrin phosphorylation was determined by autoradiography.

Figure 7:
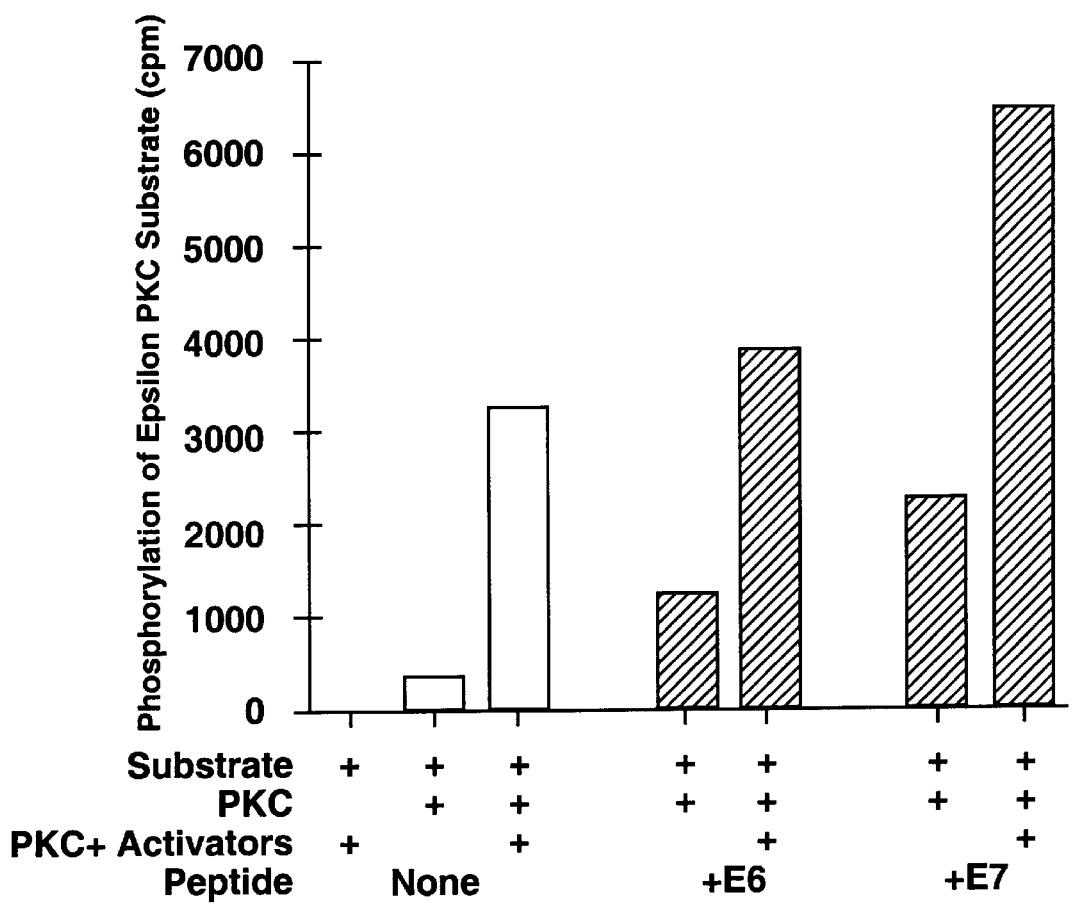
FIG. 7 shows the phosphorylation of εPKC substrate calsequestrin in the presence and/or absence of the indicated factors and peptides εV1-6 (E6; SEQ ID NO:5) and εV1-7 (E7; SEQ ID NO:6).

Exemplary results are shown in FIG. 7. As can be appreciated, the εV1-7 peptide (E7; SEQ ID NO: 6) caused an activation of εPKC as measured by its phosphorylation of the εPKC substrate calsequestrin. Catalytic activity towards histone was not measured because it is a poor substrate for this isozyme.

EXAMPLE 6

Peptide-Induced Translocation of PKC in Cardiac Myocytes

Cells were transiently permeabilized with saponin as described above in the presence of either peptide εV1-7 (SEQ ID NO:6) or peptide βC2-6 (βPKC-selective agonist; SEQ ID NO:2) and the subcellular localization of various PKC isozymes was determined. Treatment with the εV1-7 peptide (10 μg/ml in permeabilization buffer) caused translocation of εPKC in 70% of the cells (FIG. 8), whereas peptide βC2-6 (SEQ ID NO:2) did not significantly altered the localization of this isozyme from that observed in control cells. Conversely, peptide βC2-6 (SEQ ID NO:2) caused selective translocation of βPKC and not εPKC or δPKC. Therefore, peptide εV1-7 (SEQ ID NO:6) acts as a selective translocation agonist of εPKC.

EXAMPLE 7

Protection of Cardiac Myocytes by Activation of εPKC

Myocytes were transiently permeabilized with saponin as described above in the presence of εPKC-selective agonist peptide, εV1-7 (SEQ ID NO:6), βPKC specific antagonist peptide βC2-4 (SEQ ID NO:1), or in their absence. A forth group of myocytes was exposed to 30 minutes of hypoxia in the absence of glucose (PC). After 30 minutes of recovery under normoxic conditions, preconditioned cells and controls were exposed to 9 hours of hypoxia and cell viability was determined as described above. Results are average of two independent experiments.

The results are shown in FIG. 9. In the presence of peptide εV1-7 (SEQ ID NO:6), 65% of the cells were viable. In contrast, only 35% of the cells were viable in the absence of peptide εV1-7 (SEQ ID NO:6) or in the presence of the β pseudo-RACK peptide. Furthermore, equal protection from cell death by ischemia was obtained by preconditioning, indicating that εPKC activation is not only necessary for preconditioning-induced protection from ischemia, but is also sufficient.

According to the present invention, a selective agonist of εPKC as a preconditioning-mimetic agent is likely to cause fewer side effects as compared with general activators of PKC isozymes and thus has therapeutic value for protection from cardiac ischemia.

EXAMPLE 8

Effect of εV1-7 Peptide on Contraction Rate

Cells were cultured and transiently permeabilized with saponin as above in the absence or the presence of 10 μM εV1-7 (SEQ ID NO:6). Basal contraction rates were monitored to establish a baseline following permeabilization. The cells were then treated with 4βPMA (3 nM) and the rate of contraction monitored at the indicated times as previously described (Johnson and Mochly-Rosen, 1995).

The results (FIG. 10) suggest that the εPKC agonist peptide εV1-7 acts synergistically with PMA to induce εPKC-mediated effect on the slowing of contraction rate.

While the invention has been described with reference to specific methods and embodiments, it is appreciated that various modifications and changes may be made without departing from the invention.

It is claimed:

1. A peptide selected from the group consisting of SEQ ID NO:6, SEQ ID NO:7, SEQ ID NO:8, SEQ ID NO:9, SEQ ID NO:10, SEQ ID NO:12, SEQ ID NO:13, SEQ ID NO:14, SEQ ID NO:15, SEQ ID NO:16, SEQ ID NO:17, SEQ ID NO:18, and SEQ ID NO:19.

2. The peptide of claim 1 selected from the group consisting of SEQ ID NO:6, SEQ ID NO:7, SEQ ID NO:8, SEQ ID NO:9, SEQ ID NO:10, SEQ ID NO:12, SEQ ID NO:13 and SEQ ID NO:18.

3. The peptide of claim 2 selected from the group consisting of SEQ ID NO:6, SEQ ID NO:7, SEQ ID NO:8, SEQ ID NO:9, SEQ ID NO:10 and SEQ ID NO:18.

4. The peptide of claim 3 represented by SEQ ID NO:6.

5. The peptide of claim 3 represented by SEQ ID NO:7.

6. The peptide of claim 3 represented by SEQ ID NO:8.

7. The peptide of claim 1, wherein said peptide is chemically synthesized.

8. The peptide of claim 1, wherein said peptide is recombinantly produced.

9. The peptide of claim 8, wherein said peptide is encoded by a polynucleotide fragment in an expression vector.

10. A method of reducing ischemic injury to a cell exposed to hypoxia conditions, comprising
    introducing into said cell, prior to exposure to said hypoxic conditions, a pharmaceutically-effective amount of an isozyme-specific εPKC peptide agonist, wherein said pharmaceutically-effective amount of said isozyme-specific εPKC peptide agonist is effective to cause preconditioning, and said preconditioning is effective to reduce ischemic injury to said cell caused by subsequent exposure to ischemic conditions relative to the ischemic injury suffered by a cell that did not undergo preconditioning.

11. The method of claim 10, wherein said peptide is selected from the group consisting of SEQ ID NO:6, SEQ ID NO:7, SEQ ID NO:8, SEQ ID NO:9, SEQ ID NO:10, SEQ ID NO:12, SEQ ID NO:13, SEQ ID NO:14, SEQ ID NO:15, SEQ ID NO:16, SEQ ID NO:17, SEQ ID NO:18, and SEQ ID NO:19.

12. The method of claim 11, wherein said peptide is selected from the group consisting of SEQ ID NO:6 and SEQ ID NO:7.

13. The method of claim 10, wherein said cell is a cardiac cell.

14. The method of claim 10, wherein said cell is a central nervous system cell.

15. The method of claim 10, wherein said introducing includes introducing said εPKC agonist via liposome-mediated delivery.

16. A method of identifying a compound effective to induce preconditioning in a cell, comprising
    contacting an εPKC polypeptide containing a RACK binding site with an εPKC agonist peptide in the presence and absence of a test compound for inducing preconditioning in a cell,
    measuring the binding between said εPKC polypeptide and said εPKC agonist peptide in the presence and absence of said test compound, and identifying said test compound as being effective to induce preconditioning if binding in the presence of the test compound is significantly decreased relative to binding in the absence of the test compound.

17. The method of claim 16, wherein said test compound is effective to inhibit binding between the polypeptide and the agonist peptide.

18. The method of claim 16, wherein said test compound is effective to displace the agonist peptide from the polypeptide.

19. The method of claim 16, wherein said contacting includes contacting an εPKC polypeptide that is immobilized on a solid support.

20. The method of claim 16, wherein said test compound is one of a plurality of small molecules in a small molecule combinatorial library.

21. The method of claim 16, wherein said polypeptide is a full-length εPKC polypeptide.

22. The method of claim 16, wherein said polypeptide consists of εPKC amino acids 1–142.

23. The method of claim 16, wherein said agonist peptide is selected from the group consisting of SEQ ID NO:6, SEQ ID NO:7, SEQ ID NO:8, SEQ ID NO:9, SEQ ID NO:10, SEQ ID NO:12, SEQ ID NO:13, SEQ ID NO:14, SEQ ID NO:15, SEQ ID NO:16, SEQ ID NO:17, SEQ ID NO:18, and SEQ ID NO:19.

24. The method of claim 23, wherein said agonist peptide is selected from the group consisting of SEQ ID NO:6 and SEQ ID NO:7.

25. The method of claim 16, wherein said agonist peptide is fluorescently-labelled.

26. The method of claim 16, wherein said agonist peptide is radiolabelled.

27. The method of claim 16, wherein said εPKC agonist peptide is a peptide fragment derived from an εPKC-specific RACK.

* * * * *

UNITED STATES PATENT AND TRADEMARK OFFICE
CERTIFICATE OF CORRECTION

PATENT NO. : 6,165,977
APPLICATION NO. : 08/953033
DATED : December 26, 2000
INVENTOR(S) : Mochly-Rosen Page 1 of 1

It is certified that error appears in the above-identified patent and that said Letters Patent is hereby corrected as shown below:

Abstract

Please delete the Abstract and substitute the following:

--Phospholipids (e.g. MPPA and DPPS) show a remarkable antimicrobial effect against gram negative (e.g. *Pseudomonas* and *Klebsiella*) and gram positive (e.g. *Staphylococcus* and *Enterococcus*) bacteria. When the phospholipids are combined with antibiotics (e.g. ampicillin, ceftazidime or piperacillin), the effect of the antibiotic is enhanced by the presence of the phospholipid. The substance of the invention will be used alone or in combination with antibiotics, antimicrobials, antifungal, antiviral or antiprotozoal drugs for the combat of infectious diseases, such as prophylactic, cytocidal, antibacterial, bacteriostatic and/or bacteriocidal effects.--

Signed and Sealed this

Fifth Day of June, 2007

JON W. DUDAS
*Director of the United States Patent and Trademark Office*